United States Patent
Bergeron, Jr.

(10) Patent No.: US 9,730,917 B2
(45) Date of Patent: *Aug. 15, 2017

(54) DESFERRITHIOCIN POLYETHER ANALOGUES

(71) Applicant: University of Florida Research Foundation, Inc., Gainesville, FL (US)

(72) Inventor: Raymond J. Bergeron, Jr., Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 326 days.

This patent is subject to a terminal disclaimer.

(21) Appl. No.: 14/875,462

(22) Filed: Oct. 5, 2015

(65) Prior Publication Data

US 2016/0022645 A1 Jan. 28, 2016

Related U.S. Application Data

(60) Division of application No. 13/683,301, filed on Nov. 21, 2012, now Pat. No. 9,174,948, which is a continuation of application No. 12/450,194, filed as application No. PCT/US2008/003433 on Mar. 14, 2008, now Pat. No. 8,324,397.

(60) Provisional application No. 60/929,018, filed on Jun. 8, 2007, provisional application No. 60/966,539, filed on Mar. 15, 2007.

(51) Int. Cl.
*A61K 31/426* (2006.01)
*C07D 277/12* (2006.01)

(52) U.S. Cl.
CPC .......... *A61K 31/426* (2013.01); *C07D 277/12* (2013.01)

(58) Field of Classification Search
CPC .................................... A61K 31/426
USPC ........................................ 548/201
See application file for complete search history.

(56) References Cited

U.S. PATENT DOCUMENTS

| | | |
|---|---|---|
| 3,274,207 A | 9/1966 | Kollonitsch |
| 3,809,754 A | 5/1974 | Bertrand |
| 3,882,110 A | 5/1975 | Clemence et al. |
| 4,270,537 A | 6/1981 | Romaine |
| 4,367,233 A | 1/1983 | Clark et al. |
| 4,406,905 A | 9/1983 | Zahner et al. |
| 4,457,935 A | 7/1984 | Iwao et al. |
| 4,457,936 A | 7/1984 | Draeger et al. |
| 4,558,059 A | 12/1985 | Kawasaki et al. |
| 4,596,556 A | 6/1986 | Morrow et al. |
| 4,736,060 A | 4/1988 | Tomuro et al. |
| 4,775,675 A | 10/1988 | Gyorgydeak et al. |
| 4,790,824 A | 12/1988 | Morrow et al. |
| 4,886,499 A | 12/1989 | Cirelli et al. |
| 4,902,700 A | 2/1990 | Hayasi et al. |
| 4,914,208 A | 4/1990 | Jakob et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,084,083 A | 1/1992 | Lewis et al. |
| 5,106,992 A | 4/1992 | Magnin et al. |
| 5,141,496 A | 8/1992 | Dalto et al. |
| 5,169,858 A | 12/1992 | Rubin |

(Continued)

FOREIGN PATENT DOCUMENTS

| | | |
|---|---|---|
| CS | 205217 B1 | 5/1981 |
| DE | 2245560 A1 | 3/1974 |

(Continued)

OTHER PUBLICATIONS

Bergeron et al., Journal of Medicinal Chemistry, (May 4, 2006), 49(9), pp. 2772-2783.*

(Continued)

*Primary Examiner* — Laura L Stockton
(74) *Attorney, Agent, or Firm* — Wolf, Greenfield & Sacks, P.C.

(57) ABSTRACT

A relatively non-toxic desazadesferrithiocin analog having the formula:

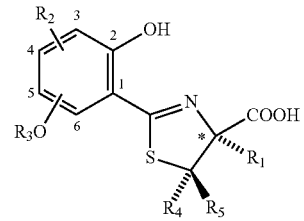

wherein: $R_1$, $R_2$, $R_4$ and $R_5$ may be the same or different and may be H, straight or branched chain alkyl having up to 14 carbon atoms, e.g., methyl, ethyl, propyl and butyl, or arylalkyl wherein the aryl portion is hydrocarbyl and the alkyl portion is straight or branched chain, the arylalkyl group having up to 14 carbon atoms, $R_2$ optionally being alkoxy having up to 14 carbon atoms;
$R_3$ is $[(CH_2)_n-O]_x-[(CH_2)_n-O]_y$-alkyl;
n is, independently, an integer from 1 to 8;
x is an integer from 1 to 8;
y is an integer from 0 to 8, and
$R_3O$ may occupy any position on the phenyl ring except the 4-position, or
a salt, hydrate or solvate thereof; and methods and compositions for treating the effects of trivalent metal, i.e., iron, overload.

47 Claims, 6 Drawing Sheets

(56) References Cited

U.S. PATENT DOCUMENTS

| | | | |
|---|---|---|---|
| 5,182,402 | A | 1/1993 | Lewis et al. |
| 5,190,521 | A | 3/1993 | Hubbard et al. |
| 5,192,781 | A | 3/1993 | Bru-Magniez et al. |
| 5,312,335 | A | 5/1994 | McKinnon et al. |
| 5,328,483 | A | 7/1994 | Jacoby |
| 5,334,144 | A | 8/1994 | Alchas et al. |
| 5,339,163 | A | 8/1994 | Homma et al. |
| 5,383,851 | A | 1/1995 | McKinnon, Jr. et al. |
| 5,385,922 | A | 1/1995 | Bron et al. |
| 5,393,777 | A | 2/1995 | Crosa |
| 5,417,662 | A | 5/1995 | Hjertman et al. |
| 5,442,073 | A | 8/1995 | Eicken et al. |
| 5,466,220 | A | 11/1995 | Brenneman |
| 5,480,381 | A | 1/1996 | Weston |
| 5,503,627 | A | 4/1996 | McKinnon et al. |
| 5,520,639 | A | 5/1996 | Peterson et al. |
| 5,527,288 | A | 6/1996 | Gross et al. |
| 5,569,189 | A | 10/1996 | Parsons |
| 5,599,302 | A | 2/1997 | Lilley et al. |
| 5,614,520 | A | 3/1997 | Kondo et al. |
| 5,649,912 | A | 7/1997 | Peterson |
| 5,704,911 | A | 1/1998 | Parsons |
| 5,840,739 | A | 11/1998 | Bergeron, Jr. |
| 5,893,397 | A | 4/1999 | Peterson et al. |
| 5,993,412 | A | 11/1999 | Deily et al. |
| 6,080,764 | A | 6/2000 | Chihiro et al. |
| 6,083,966 | A | 7/2000 | Bergeron, Jr. |
| 6,147,070 | A | 11/2000 | Facchini |
| 6,159,983 | A | 12/2000 | Bergeron, Jr. |
| 6,251,927 | B1 | 6/2001 | Lai et al. |
| 6,373,912 | B1 | 4/2002 | Yu |
| 6,437,143 | B2 | 8/2002 | Moinet et al. |
| 6,521,652 | B1 | 2/2003 | Bergeron |
| 6,525,080 | B1 | 2/2003 | Bergeron |
| 6,559,315 | B1 | 5/2003 | Bergeron |
| 6,864,270 | B2 | 3/2005 | Bergeron, Jr. |
| RE39,132 | E | 6/2006 | Bergeron, Jr. |
| 7,126,004 | B2 | 10/2006 | Bergeron |
| 7,144,904 | B2 | 12/2006 | Bergeron, Jr. |
| 7,531,563 | B2 | 5/2009 | Bergeron |
| 8,008,502 | B2 | 8/2011 | Bergeron |
| 8,063,227 | B2 | 11/2011 | Tapper et al. |
| 8,278,458 | B2 | 10/2012 | Bergeron, Jr. |
| 8,324,397 | B2 * | 12/2012 | Bergeron, Jr. ....... C07D 277/12 548/201 |
| 8,604,216 | B2 | 12/2013 | Bergeron, Jr. |
| 8,722,899 | B2 | 5/2014 | Bergeron, Jr. |
| 9,096,553 | B2 | 8/2015 | Bergeron, Jr. |
| 9,174,948 | B2 | 11/2015 | Bergeron, Jr. |
| 2002/0049316 | A1 | 4/2002 | Halbert et al. |
| 2003/0083349 | A1 | 5/2003 | Bergeron, Jr. |
| 2003/0236417 | A1 | 12/2003 | Bergeron |
| 2004/0044220 | A1 | 3/2004 | Bergeron, Jr. |
| 2004/0132789 | A1 | 7/2004 | Bergeron, Jr. |
| 2005/0033057 | A1 | 2/2005 | Bergeron |
| 2005/0234113 | A1 | 10/2005 | Bergeron |
| 2006/0211746 | A1 | 9/2006 | Bergeron |
| 2007/0238767 | A1 | 10/2007 | Bergeron |
| 2008/0214630 | A1 | 9/2008 | Bergeron |
| 2010/0093812 | A1 | 4/2010 | Bergeron, Jr. |
| 2010/0094016 | A1 | 4/2010 | Bergeron |
| 2010/0137346 | A1 | 6/2010 | Bergeron, Jr. |
| 2011/0053993 | A1 | 3/2011 | McCall, Jr. et al. |
| 2011/0275636 | A1 | 11/2011 | Malecha |
| 2012/0184586 | A1 | 7/2012 | Bergeron, Jr. |
| 2013/0030028 | A1 | 1/2013 | Bergeron, Jr. |
| 2013/0210870 | A1 | 8/2013 | Bergeron, Jr. |
| 2014/0235680 | A1 | 8/2014 | Bergeron, Jr. |
| 2014/0323534 | A1 | 10/2014 | Bergeron, Jr. |
| 2014/0343110 | A1 | 11/2014 | Bergeron, Jr. |
| 2015/0336911 | A1 | 11/2015 | Bergeron, Jr. |

FOREIGN PATENT DOCUMENTS

| | | |
|---|---|---|
| DE | 3002989 A1 | 7/1981 |
| EP | 0 214 101 A2 | 3/1987 |
| EP | 0 214 933 A2 | 3/1987 |
| EP | 0 325 559 A2 | 7/1989 |
| EP | 0 513 379 A1 | 11/1992 |
| FR | 2247243 A2 | 5/1975 |
| GB | 1292170 A | 10/1972 |
| GB | 1320534 A | 6/1973 |
| GB | 1382887 A | 2/1975 |
| JP | 57-058682 A | 4/1982 |
| WO | WO 94/11367 A1 | 5/1994 |
| WO | WO 97/13537 A1 | 4/1997 |
| WO | WO 97/36885 A1 | 10/1997 |
| WO | WO 97/37705 A1 | 10/1997 |
| WO | WO 99/34850 A1 | 7/1999 |
| WO | WO 99/53039 A1 | 10/1999 |
| WO | WO 00/12493 A1 | 3/2000 |
| WO | WO 00/16763 A2 | 3/2000 |
| WO | WO 01/27119 A2 | 4/2001 |
| WO | WO 03/078467 A1 | 9/2003 |
| WO | WO 2004/017959 A2 | 3/2004 |
| WO | WO 2005/023310 A2 | 3/2005 |
| WO | WO 2005/034949 A1 | 4/2005 |
| WO | WO 2006/055412 A1 | 5/2006 |
| WO | WO 2006/107626 A1 | 10/2006 |
| WO | WO 2008/115433 A1 | 9/2008 |
| WO | WO 2008/130395 A2 | 10/2008 |
| WO | WO 2009/053628 A2 | 4/2009 |
| WO | WO 2010/009120 A2 | 1/2010 |
| WO | WO 2011/017054 A2 | 2/2011 |
| WO | WO 2011/028255 A2 | 3/2011 |
| WO | WO 2012/027794 A2 | 3/2012 |
| WO | WO 2013/090750 A1 | 6/2013 |
| WO | WO 2013/090766 A1 | 6/2013 |

OTHER PUBLICATIONS

European Search Report, mailed Mar. 20, 2015, in connection with Application No. EP 12857135.3.

Extended European Search Report, mailed Dec. 27, 2010, in connection with Application No. EP 08742093.1.

Extended European Search Report, mailed Jan. 19, 2010, in connection with Application No. EP 07874513.0.

Extended European Search Report, mailed Jul. 9, 2015, in connection with Application No. EP 12857135.3.

Extended European Search Report, mailed Mar. 25, 2013, in connection with Application No. EP 10814064.1.

International Preliminary Examination Report, mailed Feb. 2, 2001, in connection with Application No. PCT/US1999/019691.

International Preliminary Report on Patentability, mailed Jun. 23, 2009, in connection with Application No. PCT/US2007/025377.

International Preliminary Report on Patentability, mailed Jun. 26, 2014, in connection with Application No. PCT/US2012/069795.

International Preliminary Report on Patentability, mailed Jun. 26, 2014, in connection with Application No. PCT/US2012/069826.

International Preliminary Report on Patentability, mailed Mar. 8, 2012, in connection with Application No. PCT/US2010/002336.

International Preliminary Report on Patentability, mailed Oct. 18, 2007, in connection with Application No. PCT/US2006/010945.

International Preliminary Report on Patentability, mailed Sep. 24, 2009, in connection with Application No. PCT/US2008/003433.

International Search Report and Written Opinion, mailed Apr. 12, 2013, in connection with Application No. PCT/US2012/069826.

International Search Report and Written Opinion, mailed Apr. 14, 2015, in connection with Application No. PCT/US2014/066961.

International Search Report and Written Opinion, mailed Apr. 14, 2015, in connection with Application No. PCT/US2014/066965.

International Search Report and Written Opinion, mailed Apr. 19, 2013, in connection with Application No. PCT/US2012/069795.

International Search Report and Written Opinion, mailed Aug. 9, 2006, in connection with Application No. PCT/US2006/010945.

International Search Report and Written Opinion, mailed Jan. 8, 2009, in connection with Application No. PCT/US2007/025377.

(56) References Cited

OTHER PUBLICATIONS

International Search Report and Written Opinion, mailed Jun. 19, 2008, in connection with Application No. PCT/US2008/003433.
International Search Report and Written Opinion, mailed Mar. 5, 2004, in connection with Application No. PCT/US2003/028304.
International Search Report and Written Opinion, mailed May 23, 2011, in connection with Application No. PCT/US2010/002336.
International Search Report, mailed Jan. 19, 2000, in connection with Application No. PCT/US1999/019691.
Invitation to Pay Additional Fees, mailed Jan. 27, 2015, in connection with Application No. PCT/US2014/066961.
Invitation to Pay Additional Fees, mailed Jan. 27, 2015, in connection with Application No. PCT/US2014/066965.
Supplementary European Search Report, mailed Dec. 5, 2001, in connection with Application No. EP 99945267.5.
Written Opinion, mailed Aug. 21, 2000, in connection with Application No. PCT/US1999/019691.
[No Author Listed] Highlights of Prescribing Information: EXJADE. Novartis Pharma Stein AG. 2010. Available at http://www.pharma.us.novartis.com/product/pi/pdf/exjade.pdf. Last accessed Sep. 9, 2010. 14 pages.
[No Author Listed] "Ion exchanger." Ullmanns Encyclopedia of Industrial Chemistry. 5th Ed. vol. 14A:446-56.
[No Author Listed] Databse CHEMCATS, Accession No. 2003:2524667; TimTec Overseas Stock; May 19, 2003.
[No Author Listed] Desferal. Product Information. Novartis Pharmaceuticals Corporation. East Hanover, NJ. 2011. Available at www.pharma.us.novartis.com/product/pi/pdf/desferal.pdf. Last accessed Jan. 25, 2013.
[No Author Listed], Closed head injury. Wikipedia. http://en.wikipedia.org/wiki/Close_head_injury [last accessed Nov. 28, 2011]. 7 pages.
[No Author Listed], Irritable bowel syndrome. Wikipedia. http://en.wikipedia.org/wild/Irritable_bowel_syndrome [last accessed Nov. 28, 2011]. 24 pages.
[No Author Listed], Macular degeneration. Wikipedia. http://en.wikipedia.org/wiki/Macular_degeneration [last accessed Nov. 28, 2011]. 14 pages.
[No Author Listed], Reperfusion injury. Wikipedia. http://en.wikipedia.org/wiki/Reperfusion_injury [last accessed Nov. 28, 2011]. 7 pages.
[No Author Listed], Stroke. Wikipedia. http://en.wikipedia.org/wiki/Stroke [last accessed Nov. 28, 2011]. 29 pages.
Allgayer, Clinical relevance of oxygen radicals in inflammatory bowel disease—facts and fashion. Klin Wochenschr. Dec. 15, 1991;69(21-23):1001-3.
Al-Refaie et al., Zinc concentration in patients with iron overload receiving oral iron chelator 1,2-dimethyl-3-hydroxypyrid-4-one or desferrioxamine. J Clin Pathol. 1994;47:657-60.
Anderegg et al., Metal Complex Formation of a New Siderophore Desferrithiocin and of Three Related Ligands. J Chem Soc Chem Commun. 1990:1194-6.
Angelucci et al., Hepatic iron concentration and total body iron stores in thalassemia major. N Engl J Med. Aug. 3, 2000;343(5):327 31.
Babbs et al., Oxygen radicals in ulcerative colitis. Free Radic Biol Med. 1992;13(2):169-81.
Bailly et al., Shedding of kidney injury molecule-1, a putative adhesion protein involved in renal regeneration. J Biol Chem. Oct. 18, 2002;277(42):39739-48. Epub Jul. 23, 2002.
Bartakke et al., Effect of Deferiprone on Urinary Zinc Excretion in Multiply Transfused Children with Thalassemia Major. Ind Ped. Feb. 17, 2005;42:150-4.
Berge et al., Pharmaceutical salts. J Pharm Sci. Jan. 1977;66(1):1-19.
Bergeron et al., A comparative evaluation of iron clearance models. Ann N Y Acad Sci. 1990;612:378-93.
Bergeron et al., A comparative study of the iron-clearing properties of desferrithiocin analogues with desferrioxamine B in a Cebus monkey model. Blood. Apr. 15, 1993;81(8):2166-73.
Bergeron et al., A comparison of the iron-clearing properties of 1,2-dimethyl-3-hydroxypyrid-4-one, 1,2-diethyl-3-hydroxypyrid-4-one, and deferoxamine. Blood. Apr. 1, 1992;79(7):1882-90.
Bergeron et al., An investigation of desferrithiocin metabolism. J Med Chem. Sep. 2, 1994;37(18):2889-95.
Bergeron et al., Comparison of iron chelator efficacy in iron-overloaded beagle dogs and monkeys (Cebus apella). Comp Med. Dec. 2004;54(6):664-72.
Bergeron et al., Desazadesmethyldesferrithiocin Analogues as Orally Effective Iron Chelators. J Med Chem. 1999;42:95-108.
Bergeron et al., Desferrithiocin analogue based hexacoordinate iron(III) chelators. J Med Chem. Jan. 2, 2003;46(1):16-24.
Bergeron et al., Desferrithiocin analogue iron chelators: iron clearing efficiency, tissue distribution, and renal toxicity. Biometals. Apr. 2011;24(2):239-58. Epub Nov. 20, 2010.
Bergeron et al., Desferrithiocin analogue uranium decorporation agents. Int. J Radiat Biol. Apr. 2009;85(4):348-61.
Bergeron et al., Desferrithiocin analogues and nephrotoxicity. J Med Chem. Oct. 9, 2008;51(19):5993-6004. Epub Sep. 13, 2008.
Bergeron et al., Design, synthesis, and testing of non-nephrotoxic desazadesferrithiocin polyether analogues. J Med Chem. Jul. 10, 2008;51(13):3913-23. Epub Jun. 6, 2008.
Bergeron et al., Design, Synthesis, and Testing of Polyamine Vectored Iron Chelators. Synthesis (Stuttg). 2010;2010(21):3631-3636.
Bergeron et al., Effects of C-4 stereochemistry and C-4' hydroxylation on the iron clearing efficiency and toxicity of desferrithiocin analogues. J Med Chem. Jul. 1, 1999;42(13):2432-40.
Bergeron et al., Evaluation of desferrithiocin and its synthetic analogues as orally effective iron chelators. J Med Chem. Jul. 1991;34(7):2072-8.
Bergeron et al., Evaluation of the desferrithiocin pharmacophore as a vector for hydroxamates. J Med Chem. Jul. 29, 1999;42(15):2881-6.
Bergeron et al., HBED: A Potential Alternative to Deferoxamine for Iron-Chelating Therapy. Blood. 1998;91:1446-52.
Bergeron et al., Impact of the 3,6,9-Trioxadecyloxy Group on Desazadesferrithiocin Analogue Iron Clearance and Organ Distribution. J Med Chem. Jul. 12, 2007;50(14):3302-13. Epub Jun. 12, 2007.
Bergeron et al., Impact of the Lipophilicity of Desferrithiocin Analogues on Iron Clearance. Medicinal Inorg Chem. 2005:366-83.
Bergeron et al., Influence of iron on in vivo proliferation and lethality of L1210 cells. J Nutr. Mar. 1985;115(3):369-74.
Bergeron et al., Iron chelation promoted by desazadesferrithiocin analogs: An enantioselective barrier. Chirality. Aug. 2003;15(7):593-9.
Bergeron et al., Iron Chelators and Therapeutic Uses. In: Burger's Medicinal Chemistry, 6th ed. 2003:479-561.
Bergeron et al., Metabolism and pharmacokinetics of N1,N11-diethylnorspermine in a Cebus apella primate model. Cancer Res. Aug. 15, 2000;60(16):4433-9.
Bergeron et al., Metabolism and pharmacokinetics of N1,N14-diethylhomospermine. Drug Metab Dispos. Mar. 1996;24(3):334-43.
Bergeron et al., Methoxylation of desazadesferrithiocin analogues: enhanced iron clearing efficiency. J Med Chem. Apr. 10, 2003;46(8):1470-7.
Bergeron et al., Partition-variant desferrithiocin analogues: organ targeting and increased iron clearance. J Med Chem. Feb. 10, 2005;48(3):821-31.
Bergeron et al., Pharmacokinetics of orally administered desferrithiocin analogs in cebus apella primates. Drug Metab Dispos. Dec. 1999;27(12):1496-8.
Bergeron et al., Polyamine-vectored iron chelators: the role of charge. J Med Chem. Jun. 16, 2005;48(12):4120-37.
Bergeron et al., Prevention of acetic acid-induced colitis by desferrithiocin analogs in a rat model. Dig Dis Sci. Feb. 2003;48(2):399-407.
Bergeron et al., Structure-activity relationships among desazadesferrithiocin analogues. In: Iron Chelation Therapy. Hershko, ed. 2002:167-84.

(56) References Cited

OTHER PUBLICATIONS

Bergeron et al., Substituent effects on desferrithiocin and desferrithiocin analogue iron-clearing and toxicity profiles. J Med Chem. Aug. 23, 2012;55(16):7090-103. doi: 10.1021/jm300509y. Epub Aug. 13, 2012.

Bergeron et al., Synthesis and biological evaluation of hydroxamate-based iron chelators. J Med Chem. Nov. 1991;34(11):3182-7.

Bergeron et al., Synthesis and biological evaluation of naphthyldesferrithiocin iron chelators. J Med Chem. Apr. 12, 1996;39(8):1575-81.

Bergeron et al., Synthesis of heterobactins A and B and Nocardia heterobactin. Tetrahedron. 2011;67(18):3163-69.

Bergeron et al., The desferrithiocin pharmacophore. J Med Chem. May 13, 1994;37(10):1411-7.

Bergeron et al., The design, synthesis, and evaluation of organ-specific iron chelators. J Med Chem. Nov. 30, 2006;49(24):7032-43.

Bergeron et al., The impact of polyether chain length on the iron clearing efficiency and physiochemical properties of desferrithiocin analogues. J Med Chem. Apr. 8, 2010;53(7):2843-53.

Bergeron et al., The origin of the differences in (R)- and (S)-desmethyldesferrithiocin. Iron-clearing properties. Ann N Y Acad Sci. Jun. 30, 1998;850:202-16.

Bergeron et al., Vibriobactin antibodies: a vaccine strategy. J Med Chem. Jun. 25, 2009;52(12):3801-13.

Bergeron, Desferrithiocin Polyether Analogue Uranium Decorporation Agents. Quad Chart and White Paper. Research Area #4 Radiological/Nuclear Threat Medical Countermeasures. BARDA CBRN BAA-11-100-SOL-00009. Oct. 27, 2011. 17 pages.

Bergeron, Iron: A Controlling Nutrient in Proliferative Processes. Trends in Biochem Sci. 1986;11:133-36.

Bickel et al., [Metabolic Properties of Actinomycetes.] Ferrioxamine B. Helv Chim Acta. 1960;43:2129-38. German.

Bierer et al., The effect of desferrithiocin, an oral iron chelator, on T-cell function. Blood. Nov. 15, 1990;76(10):2052-9.

Bonkovsky et al., Iron-induced liver injury. Clin Liver Dis. May 2000;4(2):409-29, vi-vii.

Bonventre, Kidney injury molecule-1 (KIM-1): a urinary biomarker and much more. Nephrol Dial Transplant. Nov. 2009;24(11):3265-8. doi: 10.1093/ndt/gfp010. Epub Mar. 23, 2009.

Brittenham et al., Efficacy of deferoxamine in preventing complications of iron overload in patients with thalassemia major. N Engl J Med. Sep. 1, 1994;331(9):567-73.

Brittenham, Disorders of Iron Metabolism: Iron Deficiency and Overload. In: Hermatology: Basic Principles and Practice. 3d Ed. Hoffman et al., eds., Churchill Livingston. New York. 2000:397-428.

Brittenham, Iron chelators and iron toxicity. Alcohol. Jun. 2003;30(2):151-8.

Brittenham, Pyridoxal isonicotinoyl hydrazone. Effective iron chelation after oral administration. Ann N Y Acad Sci. 1990;612:315-26.

Brittenham, Pyridoxal isonicotinoyl hydrazone: an effective iron-chelator after oral administration. Semin Hematol. Apr. 1990;27(2):112-6.

Brunner et al., Carboplatin-containing Porphyrin-platinum Complexes as Cytotoxic and Phototoxic Antitumor Agents. Inorg Chim Acta. 2004;357:4423-51.

Byers et al., Microbial iron transport: iron acquisition by pathogenic microorganisms. Met Ions Biol Syst. 1998;35:37-66.

Caira et al., Crystalline Polymorphism of Organic Compounds. Topics in Current Chemistry. 1998;198:163-208.

Cappellini, Iron-chelating therapy with the new oral agent ICL670 (Exjade). Best Pract Res Clin Haematol. Jun. 2005;18(2):289-98.

Cario, Insulin sensitivity and beta-cell secretion in thalassaemia major with secondary haemochromatosis: assessment by oral glucose tolerance test. Eur J Pediatr. Mar. 2003;162(3):139-46. Epub Jan. 15, 2003.

Conrad et al., Iron absorption and transport. Am J Med Sci. Oct. 1999;318(4):213-29.

Cragg et al., The iron chelator L1 potentiates oxidative DNA damage in iron-loaded liver cells. Blood. Jul. 15, 1998;92(2):632-8.

Dean et al., The Action of Nine Chelators on Iron-Dependent Radical Damage. Free Rad Res. 1994;20(2):83-101.

Domingo et al., Comparative effects of the chelators sodium 4,5-dihydroxybenzene-1,3-disulfonate (Tiron) and diethylenetriaminepentaacetic acid (DTPA) on acute uranium nephrotoxicity in rats. Toxicology. Mar. 14, 1997;118(1):49-59.

Donovan et al., Preclinical and clinical development of deferitrin, a novel, orally available iron chelator. Ann N Y Acad Sci. 2005;1054:492-4.

Dunaief et al., Macular degeneration in a patient with aceruloplasminemia, a disease associated with retinal iron overload. Ophthalmology. Jun. 2005;112(6):1062-5.

Dunaief, Iron induced oxidative damage as a potential factor in age-related macular degeneration: the Cogan Lecture. Invest Ophthalmol Vis Sci. Nov. 2006;47(11):4660-4.

Durbin et al., Chelating agents for uranium(VI): 2. Efficacy and toxicity of tetradentate catecholate and hydroxypyridinonate ligands in mice. Health Phys. May 2000;78(5):511-21.

Durbin et al., In Vivo Chelation of Am(III), Pu(IV), Np(V), and U(VI) in Mice by TREN-(Me-3,2-HOPO). Radiat Prot Dosimetry. 1994;53:305-09.

Durbin, Lauriston S. Taylor Lecture: the quest for therapeutic actinide chelators. Health Phys. Nov. 2008;95(5):465-92.

Farcasiu et al., Geometrical inversion of methoxymethyl cations. J Chem Soc Chem Commun. 1979;24:1124-5.

Farkas et al., Structure-based differences between the metal ion selectivity of two siderophores desferrioxamine B (DFB) and desferricoprogen (DFC): Why DFC is much better Pb(II) sequestering agent than DFB? J Inorg Biochem. 2008;102;1654-9.

Feau et al., Preparation and Optical Properties of Novel 3-Alkoxycarbonyl Aza- and Diazacoumarins. Synth Commun. 2010;40:3033-45.

Fedorak et al., Misoprostol provides a colonic mucosal protective effect during acetic acid-induced colitis in rats. Gastroenterology. Mar. 1990;98(3):615-25.

Finch et al., Ferrokinetics in man. Medicine (Baltimore). Jan. 1970;49(1):17-53.

Finch et al., Iron metabolism. Clin Physiol Biochem. 1986;4(1):5-10.

Finch et al., Perspectives in iron metabolism. N Engl J Med. Jun. 24, 1982;306(25):1520-8.

Fossheim et al., Lanthanide-based susceptibility contrast agents: assessment of the magnetic properties. Magn Reson Med. Feb. 1996;35(2):201-6.

Fritsch et al., Plasmodium falciparum: inhibition in vitro with lactoferrin, desferriferrithiocin, and desferricrocin. Exp Parasitol. Feb. 1987;63(1):1-9.

Fukuda, Chelating agents used for plutonium and uranium removal in radiation emergency medicine. Curr Med Chem. 2005;12(23):2765-70.

Galanello et al., A dose escalation study of the pharmacokinetics, safety & efficacy of deferitrin, an oral iron chelator in beta thalassaemia patients. ASH Annu Meet Abstr. 2007;110: Abstract 2669.

Galanello et al., Safety, tolerability, and pharmacokinetics of ICL670, a new orally active iron-chelating agent in patients with transfusion-dependent iron overload due to beta-thalassemia. J Clin Pharmacol. Jun. 2003;43(6):565-72.

Galey et al., N,N'-bis-(3,4,5-trimethoxybenzyl) ethylenediamine N,N'-diacetic acid as a new iron chelator with potential medicinal applications against oxidative stress. Biochem Pharmacol. Jan. 26, 1996;51(2):103-15.

Ganguly et al., Antiviral activity of isoquinolines carbazoles and other miscellaneous synthetic chemicals in mice. Indian J Med Res. Oct. 1975;63(10):1418-25.

Giardina et al., Chelation therapy in beta-thalassemia: an optimistic update. Semin Hematol. Oct. 2001;38(4):360-6.

Golub et al., Molecular classification of cancer: class discovery and class prediction by gene expression monitoring. Science. Oct. 15, 1999;286(5439):531-7.

(56) References Cited

OTHER PUBLICATIONS

Goodsaid et al., Novel biomarkers of acute kidney toxicity. Clin Pharmacol Ther. Nov. 2009;86(5):490-6. doi: 10.1038/clpt.2009.149. Epub Aug. 26, 2009.
Gorden et al., Rational design of sequestering agents for plutonium and other actinides.Chem Rev. Nov. 2003;103(11):4207-82.
Grady et al., HBED: a potential oral iron chelator. Ann N Y Acad Sci. 1990;612:361-8.
Grady et al., Rhodotorulic acid—investigation of its potential as an iron-chelating drug. J Pharmacol Exp Ther. Jun. 1979;209(3):342-8.
Graf et al., Iron-catalyzed hydroxyl radical formation. Stringent requirement for free iron coordination site. J Biol Chem. Mar. 25, 1984;259(6):3620-4.
Grishman et al., Neutrophil-mediated mucosal injury. Role of reactive oxygen metabolites. Dig Dis Sci. Mar. 1988;33(3 Suppl):6S-15S.
Guilmette et al., Competitive binding of Pu and Am with bone mineral and novel chelating agents. Radiat Prot Dosimetry. 2003;105(1-4):527-34.
Guterman et al., Feasibility of enterochelin as an iron-chelating drug: studies with human serum and a mouse model system. Gen Pharmacol. 1978;9(2):123-7.
Hadziahmetovic et al., The oral iron chelator deferiprone protects against iron overload-induced retinal degeneration. Invest Ophthalmol Vis Sci. Feb. 16, 2011;52(2):959-68. doi: 10.1167/iovs.10-6207.
Hahn et al., Coordination Chemistry of Microbial Iron Transport. 42. Structural and Spectroscopic Characterization of Diastereomeric Cr(III) and Co(III) Complexes of Desferriferrithiocin. J Am Chem Soc. 1990;112:1854-60.
Hallberg, Bioavailability of dietary iron in man. Ann Rev Nutr. 1981;1:123-47.
Halliwell, Free radicals and antioxidants: a personal view. Nutr Rev. Aug. 1994;52(8 Pt 1):253-65.
Halliwell, Iron, Oxidative Damage and Chelating Agents. In: The Development of Iron Chelators for Clinical Use, Bergeron, ed. 1994:33-56.
Han et al., Kidney Injury Molecule-1 (KIM-1): a novel biomarker for human renal proximal tubule injury. Kidney Int. Jul. 2002;62(1):237-44.
Hazen et al., Human neutrophils employ the myeloperoxidase-hydrogen peroxide-chloride system to oxidize alpha-amino acids to a family of reactive aldehydes. Mechanistic studies identifying labile intermediates along the reaction pathway. J Biol Chem. Feb. 27, 1998;273(9):4997-5005.
Henry, Chemotherapeutic nitroheterocycles. Derivatives of 5-nitrothiazole-2-carboxaldehyde and 5-nitrothiazole-2-carboxylic acid. J Med Chem. Mar. 1969;12(2):303-6.
Hoffbrand et al., Long-term trial of deferiprone in 51 transfusion-dependent iron overloaded patients. Blood. Jan. 1, 1998;91(1):295-300.
Hoffbrand, Transfusion Siderosis and Chelation Therapy. Iron in Biochemistry and Medicine. vol. II. London. 1980: 449-527.
Hoffmann et al., Evaluation of a urinary kidney biomarker panel in rat models of acute and subchronic nephrotoxicity. Toxicology. Nov. 9, 2010;277(1-3):49-58. doi: 10.1016/j.tox.2010.08.013. Epub Sep. 9, 2010.
Horackova et al., The antioxidant effects of a novel iron chelator salicylaldehyde isonicotinoyl hydrazone in the prevention of $H_2O_2$ injury in adult cardiomyocytes. Cardiovasc Res. Aug. 18, 2000;47(3):529-36.
Hua et al., Long-term effects of experimental intracerebral hemorrhage: the role of iron. J Neurosurg. Feb. 2006;104(2):305-12.
Iranmanesh et al., Chelation of chromium(VI) by combining deferasirox and deferiprone in rats. Biometals. 2013;26:465-71.
Jalal et al., Structure of Anguibactin, a Unique Plasmid-Related Bacterial Siderophore from the Fish Pathogen Vibrio Anguillarum. J Am Chem Soc. 1989;111(1):292-96.

Jarvis et al., Some correlations involving the stability of complexes of transuranium metal ions and ligands with negatively charged oxygen donors. Inorg Chim Acta. 1991;182:229-32.
Kalinowski et al., The evolution of iron chelators for the treatment of iron overload disease and cancer. Pharmacol Rev. Dec. 2005;57(4):547-83.
Kersten et al., Long-term treatment of transfusional iron overload with the oral iron chelator deferiprone (L1): a Dutch multicenter trial. Ann Hematol. Nov. 1996;73(5):247-52.
Kicic et al., The desferrithiocin (DFT) class of iron chelators: potential as antineoplastic agents. Anticancer Drug Des. Aug.-Oct. 2001;16(4-5):195-207.
Kishore et al., Synthesis of α-Poly-[Nε-2-aryl-Δ2-thiazoline-4-carbonyl-L-lysine] with Antival Activity. Ind J Chem. 1977;15B:255-57.
Kitazawa et al., Reduction of ultraviolet light-induced oxidative stress by amino acid-based iron chelators. Biochim Biophys Acta. Dec. 27, 1999;1473(2-3):400-8.
Kitto et al., Post-modification of Helical Dipeptido Polyisocyanides Using the "Click" Reaction. J Mater Chem. 2008;18:5615-24.
Kontoghiorghes et al., 1,2-Dimethyl-3-hydroxypyrid-4-one, an orally active chelator for treatment of iron overload. Lancet. Jun. 6, 1987;1(8545):1294-5.
Kontoghiorghes, New Concepts of Iron and Aluminium Chelation Therapy With Oral L1 (Deferiprone) and Other Chelators. Analyst. Mar. 1995;120:845-51.
Koppenol, Kinetics and Mechanisms of the Fenton Reaction: Implications in Iron Toxicity. In: Iron Chelators: New Development Strategies, Bergeron, ed., 2000:3-10.
Langer et al., Solid complexes with tetravalent metal ions and ethylenediamime tetra-acetic acid (EDTA). J Inorg Nucl Chem. 1964;26:59-72.
Levien et al., Pentetate Calcium Trisodium (Ca-DTPA) and Pentetate Zinc Trisodium (Zn-DTPA) Formulary Drug Reviews. 2005;40:65-71.
Li et al., Synthesis of Coumarin-Appended Pyridyl Tricarbonylrhenium(I) 2,2'-Bipyridyl Complexes with Oligoether Spacer and Their Fluorescence Resonance Energy Transfer Studies. Organometallics. 2009;28(6):1620-1630.
Lieu et al., The roles of iron in health and disease. Mol Aspects Med. Feb.-Apr. 2001;22(1-2):1-87.
Liu et al., Nanoparticle and iron chelators as a potential novel Alzheimer therapy. Methods Mol Biol. 2010;610:123-44. doi: 10.1007/978-1-60327-029-8_8.
Lovejoy et al., Iron chelators as anti-neoplastic agents: current developments and promise of the PIH class of chelators. Curr Med Chem. Jun. 2003;10(12):1035-49.
Luciani et al., Americium in the beagle dog: biokinetic and dosimetric model. Health Phys. May 2006;90(5):459-70.
Macpherson et al., Experimental production of diffuse colitis in rats. Digestion. 1978;17(2):135-50.
Malcovati, Impact of transfusion dependency and secondary iron overload on the survival of patients with myelodysplastic syndromes. Leuk Res. Dec. 2007;31 Suppl 3:S2-6.
Malluche et al., The Use of Deferoxamine in the Management of Aluminum Accumulation in Bone in Patients with Renal Failure. N Engl J Med. Jul. 19, 1984;311(3):140-4.
Marriott et al., Synthesis of the farnesyl ether 2,3,5-trifluoro-6-hydroxy-4-[(E,E)-3,7,11-trimethyldodeca-2,6,10-trien-1-yloxy]nitrobenzene, and related compounds containing a substituted hydroxytrifluorophenyl residue: novel inhibitors of protein farnesyltransferase, geranylgeranyltransferase I and squalene synthase. J Chem Soc Perkin Trans 1. 2000;1(24):4265-78.
Millan et al., Biological signatures of brain damage associated with high serum ferritin levels in patients with acute ischemic stroke and thrombolytic treatment. Dis Markers. 2008;25(3):181-8.
Miller et al., Efficacy of orally administered amphipathic polyaminocarboxylic acid chelators for the removal of plutonium and americium: comparison with injected Zn-DTPA in the rat. Radiat Prot Dosimetry. 2006;118(4):412-20. Epub Dec. 6, 2005.
Molina-Jijón et al., Deferoxamine pretreatment prevents Cr(VI)-induced nephrotoxicity and oxidant stress: Role of Cr(VI) chelation. Toxicol. 2012;291:93-101.

(56) References Cited

OTHER PUBLICATIONS

Naegeli et al., Metabolites of Microorganisms. Part 193. Ferrithiocin. Helv Chim Acta. 1980;63:1400-06. German.

Nash et al., Features of the thermodynamics of two-phase distribution reactions of americium(III) and europium(III) nitrates into solutions of 2,6-bis[(bis(2-ethylhexyl)phosphino)methyl]pyridine N,P,P' trioxide. Inorg Chem. Nov. 4, 2002;41(22):5849-58.

Neu et al., Structural Characterization of a Plutonium(IV) Siderophore Complex: Single-Crystal Structure of Pu-Desferrioxamine E. Angew Chem Int Ed Engl. Apr. 2000;39(8):1442-1444.

Nisbet-Brown et al., Effectiveness and safety of ICL670 in iron-loaded patients with thalassaemia: a randomised, double-blind, placebo-controlled, dose-escalation trial. Lancet. May 10, 2003;361(9369):1597-602.

O'Connell et al., The role of iron in ferritin- and haemosiderin-mediated lipid peroxidation in liposomes. Biochem J. Jul. 1, 1985;229(1):135-9.

Olivieri et al., Iron-chelating therapy and the treatment of thalassemia. Blood. Feb. 1, 1997;89(3):739-61.

Olivieri et al., Long-term safety and effectiveness of iron-chelation therapy with deferiprone for thalassemia major. N Engl J Med. Aug. 13, 1998;339(7):417-23.

Olivieri, Long-term therapy with deferiprone. Acta Haematol. 1996;95(1):37-48.

Olivieri, Progression of iron overload in sickle cell disease. Semin Hematol. Jan. 2001;38(1 Suppl 1):57-62.

Ornelas et al., An Efficient Synthesis of Highly Functionalized Chiral Lactams. Tetrahedron Lett. 2011;52:4760-63.

Østergaard et al., Evalution of capillary electrophoresis-frontal analysis for the study of low molecular weight drug-human serum albumin interactions. Electrophoresis. Sep. 2002;23(17):2842-53.

Panter et al., Dextran-Coupled Deferoxamine Improves Outcome in a Murine Model of Head Injury. J Neurotrauma. 1992;9(1):47-53.

Paquet et al., Efficacy of 3,4,3-LI(1,2-HOPO) for decorporation of Pu, Am and U from rats injected intramuscularly with high-fired particles of MOX. Radiat Prot Dosimetry. 2003;105(1-4):521-5.

Pashalidis et al., Effective complex formation in the interaction of 1,2-dimethyl-3-hydroxypyrid-4-one (Deferiprone or L1) with uranium (VI). J Radioanal Nucl Chem. 1999;242:181-84.

Pietrangelo, Iron chelation beyond transfusion iron overload. Am J Hematol. Dec. 2007;82(12 Suppl):1142-6.

Pietrangelo, Mechanism of iron toxicity. In: Iron Chelation Therapy. Hershko, ed. 2002:19-43.

Pippard et al., Iron chelation using subcutaneous infusions of diethylene triamine penta-acetic acid (DTPA). Scand J Haematol. May 1986;36(5):466-72.

Pippard, Desferrioxamine-induced iron excretion in humans. Baillieres Clin Haematol. Apr. 1989;2(2):323-43.

Pippard, Iron overload and iron chelation therapy in thalassaemia and sickle cell haemoglobinopathies. Acta Haematol. 1987;78(2-3):206-11.

Piyamongkol et al., Novel Synthetic Approach to 2-(1'-Hydroxyalkyl)- and 2-Amido-3-Hydroxypyridin-4-ones. Tetranderon. 2001;57:3479-86.

Ponka et al., Function and regulation of transferrin and ferritin. Semin Hematol. Jan. 1998;35(1):35-54.

Ponka et al., Mobilization of iron from reticulocytes. Identification of pyridoxal isonicotinoyl hydrazone as a new iron chelating agent. FEBS Lett. Jan. 15, 1979;97(2):317-21.

Rao et al., Complexation of Thorium(IV) with Desmethyldesferrithiocin. Radiochim Acta. 2000;88:851-56.

Raymond et al., Coordination Chemistry and Microbial Iron Transport. Acc Chem Res. 1979;12:183-190.

Re et al., Antioxidant activity applying an improved ABTS radical cation decolorization assay. Free Radic Biol Med. May 1999;26(9-10):1231-7.

Richardson, The controversial role of deferiprone in the treatment of thalassemia. J Lab Clin Med. May 2001;137(5):324-9.

Saljooghi et al., Clinical evaluation of Deferasirox for removal of cadmium ions in rat. Biometals. 2010;23:707-12.

Saljooghi, Chelation of aluminum by combining deferasirox and deferiprone in rats. Toxicol Ind Health. 2012;28(8):740-5.

Santos et al., A cyclohexane-1, 2-diyldinitrilotetraacetate tetrahydroxamate derivative for actinide complexation: Synthesis and complexation studies. J Chem Soc Dalton Trans. 2000:4398-4402.

Seligman et al., Molecular Mechanisms of Iron Metabolism. The Molecular Basis of Blood Diseases. 1987;219-44.

Shin et al., A novel trivalent cation chelator Feralex dissociates binding of aluminum and iron associated with hyperphosphorylated τ of Alzheimer's disease. Brain Res. 2003;961:139-46.

Souillac et al., "Characterization of Deliver Systems, Differential Scanning in Calorimetry." Encyclopedia of Controlled Drug Delivery. John Wiley & Sons. 1999:212-27.

Stahel et al., Iron chelators: in vitro inhibitory effect on the liver stage of rodent and human malaria. Am J Trop Med Hyg. Sep. 1988;39(3):236-40.

Stradling et al., Recent developments in the decorpoartion of plutonium, americium and thorium. Radiat Prot Dosimetry. 1998;79:445-48.

Streiff et al., Phase 1 study of N1-N11-diethylnorspermine (DENSPM) administered TID for 6 days in patients with advanced malignancies. Invest New Drugs. 2001;19(1):29-39.

Supkowski et al., Displacement of Inner-Sphere Water Molecules from Eu(3+) Analogues of Gd(3+) MRI Contrast Agents by Carbonate and Phosphate Anions: Dissociation Constants from Luminescence Data in the Rapid-Exchange Limit. Inorg Chem. Nov. 29, 1999;38(24):5616-5619.

Taetle et al., Combination iron depletion therapy. J Natl Cancer Inst. Aug. 16, 1989;81(16):1229-35.

Tang et al., High-resolution magnetic resonance imaging tracks changes in organ and tissue mass in obese and aging rats. Am J Physiol Regul Integr Comp Physiol. Mar. 2002;282(3):R890-9.

Theil et al., Ferritin Mineralization: Ferroxidation and Beyond. J Inorg Biochem. 1997;67:30. Abstract B13.

Thomas et al., Ferritin and superoxide-dependent lipid peroxidation. J Biol Chem. Mar. 25, 1985;260(6):3275-80.

Thompson et al., Protein conformational misfolding and amyloid formation: characteristics of a new class of disorders that include Alzheimer's and Prion diseases. Curr Med Chem. Oct. 2002;9(19):1751-62.

Trokowski et al., Cyclen-based phenylboronate ligands and their Eu3+ complexes for sensing glucose by MRI. Bioconjug Chem. Nov.-Dec. 2004;15(6):1431-40.

Uhlir et al., Specific sequestering agents for the actinides. 21. Synthesis and initial biological testing of octadentate mixed catecholate-hydroxypyridinonate ligands. J Med Chem. Feb. 19, 1993;36(4):504-9.

Vaidya et al., A rapid urine test for early detection of kidney injury. Kidney Int. Jul. 2009;76(1):108-14. doi: 10.1038/ki.2009.96. Epub Apr. 22, 2009.

Vaidya et al., Urinary kidney injury molecule-1: a sensitive quantitative biomarker for early detection of kidney tubular injury. Am J Physiol Renal Physiol. Feb. 2006;290(2):F517-29. Epub Sep. 20, 2005.

Vichinsky, Current issues with blood transfusions in sickle cell disease. Semin Hematol. Jan. 2001;38(1 Suppl 1):14-22.

Vippagunta et al., Crystalline solids. Adv Drug Deliv Rev. May 16, 2001;48(1):3-26.

Weintraub et al., The treatment of hemochromatosis by phlebotomy. Med Clin North Am. Nov. 1966;50(6):1579-90.

Whisenhunt et al., Specific Sequestering Agents for the Actinides. 29. Stability of the Thorium(IV) Complexes of Desferrioxamine B (DFO) and Three Octadentate Catecholate or Hydroxypyridinonate DFO Derivatives: DFOMTA, DFOCAMC, and DFO-1,2-HOPO. Comparative Stability of the Plutonium(IV) DFOMTA Complex(1). Inorg Chem. Jul. 3, 1996;35(14):4128-4136.

White et al., The effect of chelating agents on cellular iron metabolism. Clin Sci Mol Med. Mar. 1976;50(3):145-52.

White et al., The effect of chelating agents on iron mobilization in Chang cell cultures. Blood. Dec. 1976;48(6):923-9.

(56) References Cited

OTHER PUBLICATIONS

White et al., Total synthesis of geodiamolide A, a novel cyclodepsipeptide of marine origin. J Org Chem. 1989;54(4):736-738.
Wilen et al., Strategies in Optical Resolution. Tetrahedron. 1977;33:2725-36.
Woessner et al., Numerical solution of the Bloch equations provides insights into the optimum design of PARACEST agents for MRI. Magn Reson Med. Apr. 2005;53(4):790-9.
Wojcik et al., Natural history of C282Y homozygotes for hemochromatosis. Can J Gastroenterol. May 2002;16(5):297-302.
Wolfe et al., A non-human primate model for the study of oral iron chelators. Br J Haematol. Jul. 1989;72(3):456-61.
Wolff et al., A Phase II study of the polyamine analog N1,N11-diethylnorspermine (DENSpm) daily for five days every 21 days in patients with previously treated metastatic breast cancer. Clin Cancer Res. Dec. 1, 2003;9(16 Pt 1):5922-8.
Wood et al., The metabolism of iron-dextran given as a total-dose infusion to iron deficient Jamaican subjects. Br J Hacmatol. Feb. 1968;14(2).119-29.
Yamada et al., Role of neutrophil-derived oxidants in the pathogenesis of intestinal inflammation. Klin Wochenschr. Dec. 15, 1991;69(21-23):988-94.
Zacharski et al., Reduction of iron stores and cardiovascular outcomes in patients with peripheral arterial disease: a randomized controlled trial. JAMA. Feb. 14, 2007;297(6):603-10.
Zaman et al., Protection from oxidative stress-induced apoptosis in cortical neuronal cultures by iron chelators is associated with enhanced DNA binding of hypoxia-inducible factor-1 and ATF-1/CREB and increased expression of glycolytic enzymes, p21(waf1/cip1), and erythropoietin. J Neurosci. Nov. 15, 1999;19(22):9821-30.
Zecca et al., Neuromelanin can protect against iron-mediated oxidative damage in system modeling iron overload of brain aging and Parkinson's disease. J Neurochem. Aug. 2008;106(4):1866-75. Epub Jul. 4, 2008.
Zhang et al., A novel europium(III)-based MRI contrast agent. J Am Chem Soc. Feb. 21, 2001;123(7):1517-8.
Zhang et al., A paramagnetic CEST agent for imaging glucose by MRI. J Am Chem Soc. Dec. 17, 2003;125(50):15288-9.
Zhou et al., Comparison of kidney injury molecule-1 and other nephrotoxicity biomarkers in urine and kidney following acute exposure to gentamicin, mercury, and chromium. Toxicol Sci. Jan. 2008;101(1):159-70. Epub Oct. 13, 2007.
Zurlo et al., Survival and causes of death in thalassaemia major. Lancet. Jul. 1, 1989;2(8653):27-30.
International Search Report and Written Opinion, mailed Feb. 25, 2016, in connection with Application No. PCT/US2015/065985.
Boddaert et al., Selective iron chelation in Friedreich ataxia: biologic and clinical implications. Blood. Jul. 1, 2007;110(1):401-8. Epub Mar. 22, 2007.
Richardson et al., Development of potential iron chelators for the treatment of Friedreich's ataxia: ligands that mobilize mitochondrial iron. Biochim Biophys Acta. May 31, 2001;1536(2-3):133-40.
Wong et al., The Friedreich's ataxia mutation confers cellular sensitivity to oxidant stress which is rescued by chelators of iron and calcium and inhibitors of apoptosis. Hum Mol Genet. Mar. 1999;8(3):425-30.

\* cited by examiner

| $^1$H Assignment (9) | (multiplicity, integration, coupling constant in Hz) |
|---|---|
| a | 1.77 (s, 3 H) |
| b | 3.35 (s, 3 H) |
| c | 3.56-3.62 (m, 3 H) |
| d | 3.64-3.68 (m, 2 H) |
| d | 3.68-3.73 (m, 2 H) |
| d | 3.75-3.89 (m, 2 H) |
| e | 3.92-3.96 (m, 2 H) |
| f | 3.99 (d, 1 H, J = 11.6) |
| g | 4.25-4.31 (m, 2 H) |
| h | 6.99 (t, 1 H, J = 8.2) |
| i | 7.26-7.33 (two d, 2 H) |

¹H Assignment (12)        (multiplicity, integration, coupling constant in Hz)

a     1.27 (d, 3 H, J = 6.3)
a     1.29 (d, 3 H, J = 6.3)
b     1.66 (s, 3 H)
c     3.23 (d, 1 H, J = 11.3)
d     3.38 (s, 3 H)
e     3.53-3.58 (m, 2 H)
e     3.64-3.67 (m, 2 H)
e     3.68-3.71 (m, 2 H)
e     3.72-3.76 (m, 2 H)
f     3.84 (t, 2 H, J = 4.7)
g     3.87 (d, 1 H, J = 11.4)
h     4.10 (t, 2 H, J = 4.7)
i     5.09 (septet, 1 H, J = 6.2)
j     6.91-6.96 (two d, 2 H)
k     7.01 (dd, 1 H, J = 9.2, 3.2)
l     12.02 (br s, 1 H)

Scheme 1.

Scheme 2.

DESFERRITHIOCIN POLYETHER ANALOGUES

RELATED APPLICATIONS

This application is a divisional of and claims priority under 35 U.S.C. §120 to U.S. Application, U.S. Ser. No. 13/683,301, entitled "DESFERRITHIOCIN POLYETHER ANALOGUES," filed Nov. 21, 2012, which is a continuation of and claims priority under 35 U.S.C. §120 to U.S. Application, U.S. Ser. No. 12/450,194, entitled "DESFERRITHIOCIN POLYETHER ANALOGUES," filed on Dec. 14, 2009, which is a national stage filing under 35 U.S.C. §371 of international PCT Application, PCT/US2008/003433, designating the United States and filed on Mar. 14, 2008, which claims priority under 35 U.S.C. §119(e) to U.S. Provisional applications, U.S. Ser. No. 60/966,539, entitled "DESFERRITHIOCIN POLYETHER ANALOGUES," filed on Mar. 15, 2007, and U.S. Ser. No. 60/929,018, entitled "DESFERRITHIOCIN POLYETHER ANALOGUES," filed on Jun. 8, 2007, each of which is incorporated herein by reference.

GOVERNMENT SUPPORT

This invention was made with government support under grant No. DK49108 awarded by the National Institutes of Health. The government has certain rights in the invention.

BACKGROUND OF THE INVENTION

Humans have evolved a highly efficient iron management system in which we absorb and excrete only about 1 mg of the metal daily; there is no mechanism for the excretion of excess iron [Brittenham, G. M. Disorders of Iron Metabolism: Iron Deficiency and Overload. In Hematology: Basic Principles and Practice; 3rd ed.; Hoffman, R., Benz, E. J., Shattil, S. J., Furie, B., Cohen, H. J. et al., Eds.; Churchill Livingstone: New York, 2000; pp 397-428]. Whether derived from transfused red blood cells [Olivieri, N. F. and Brittenham, G. M. Iron-chelating Therapy and the Treatment of Thalassemia. Blood 1997, 89, 739-761; Vichinsky, E. P. Current Issues with Blood Transfusions in Sickle Cell Disease. Semin. Hematol. 2001, 38, 14-22; Kersten, M. J., Lange, R., Smeets, M. E., Vreugdenhil, G., Roozendaal, K. J., Lameijer, W. and Goudsmit, R. Long-Term Treatment of Transfusional Iron Overload with the Oral Iron Chelator Deferiprone (L1): A Dutch Multicenter Trial. Ann. Hematol. 1996, 73, 247-252] or from increased absorption of dietary iron iron [Conrad, M. E.; Umbreit, J. N.; Moore, E. G. Iron Absorption and Transport. Am. J. Med. Sci. 1999, 318, 213-229; Lieu, P. T.; Heiskala, M.; Peterson, P. A; Yang, Y. The Roles of Iron in Health and Disease, Mol. Aspects Med. 2001, 22, 1-87], without effective treatment, body iron progressively increases with deposition in the liver, heart, pancreas, and elsewhere. Iron accumulation eventually produces (i) liver disease that may progress to cirrhosis [Angelucci, E.; Brittenham, G. M.; McLaren, C. E.; Ripalti, M.; Baronciani, D.; Giardini, C.; Galimberti, M.; Polchi, P.; Lucarelli, G. Hepatic Iron Concentration and Total Body Iron Stores in Thalassemia Major. N. Engl. J. Med. 2000, 343, 327-331; Bonkovsky, H. L.; Lambrecht, R. W. Iron-Induced Liver Injury. Clin. Liver Dis. 2000, 4, 409429, vi-vii; Pietrangelo, A Mechanism of Iron Toxicity. Adv. Exp. Med. Biol. 2002, 509, 19-43], (ii) diabetes related both to iron-induced decreases in pancreatic β-cell secretion and to increases in hepatic insulin resistance [Cario, H.; Holl, R. W.; Debatin, K. M.; Kohne, E. Insulin Sensitivity and p-Cell Secretion in Thalassaemia Major with Secondary Haemochromatosis: Assessment by Oral Glucose Tolerance Test. Eur. J. Pediatr. 2003, 162, 139-146; Wojcik, J. P.; Speechley, M. R.; Kertesz, A E.; Chakrabarti, S.; Adams, P. C. Natural History of C282Y Homozygotes for Hemochromatosis. Can. J. Gastroenterol. 2002, 16, 297-302], and (iii) heart disease, still the leading cause of death in thalassemia major and related forms of transfusional iron overload [Brittenham, G. M. Disorders of Iron Metabolism: Iron Deficiency and Overload. In Hematology: Basic Principles and Practice; 3rd ed.; Hoffman, R., Benz, E. J., Shattil, S. J., Furie, B., Cohen, H. J. et al., Eds.; Churchill Livingstone: New York, 2000; pp 397-428; Brittenham, G. M.; Griffith, P. M.; Nienhuis, A W.; McLaren, C. E.; Young, N. S.; Tucker, E. E.; Allen, C. J.; Farrell, D. E.; Harris, J. W. Efficacy of Deferoxamine in Preventing Complications of Iron Overload in Patients with Thalassemia Major. N. Engl. J. Med. 1994, 331, 567-573; Zurlo, M. G.; De Stefano, P.; Borgna-Pignatti, C.; Di Palma, A.; Piga, A.; Melevendi, C.; Di Gregorio, F.; Burattini, M. G.; Terzoli, S. Survival and Causes of Death in Thalassaemia Major. Lancet 1989, 2, 27-30].

Although iron comprises 5% of the earth's crust, living systems have great difficulty in accessing and managing this vital micronutrient. The low solubility of Fe(III) hydroxide ($K_{sp}=1\times10^{-39}$) [Raymond, K. N.; Carrano, C. J. Coordination Chemistry and Microbial Iron Transport. Ace. Chem. Res. 1979, 12, 183-190], the predominant form of the metal in the biosphere, has led to the development of sophisticated iron storage and transport systems in nature. Microorganisms utilize low molecular weight, virtually ferric ion-specific ligands, siderophores [Byers, B. R; Arceneaux, J. E. Microbial Iron Transport: Iron Acquisition by Pathogenic Microorganisms. Met. Ions Biol. Syst. 1998, 35, 37-66; Kalinowski, D. S.; Richardson, D. R. The Evolution of Iron Chelators for the Treatment of Iron Overload Disease and Cancer. Pharmacol Rev. 2005, 57, 547-583.]; higher eukaryotes tend to employ proteins to transport and store iron (e.g., transferrin and ferritin, respectively) [Bergeron, R. J. Iron: A Controlling Nutrient in Proliferative Processes. Trends Biochem. Sci. 1986, 11, 133-136; Theil, E. c.; Huynh, B. H. Ferritin Mineralization: Ferroxidation and Beyond. J. Inorg. Biochem. 1997, 67, 30; Ponka, P.; Beaumont, c.; Richardson, D. R. Function and Regulation of Transferrin and Ferritin, Semin. Hematol. 1998, 35, 35-54]. In humans, nontransferrin-bound plasma iron, a heterogeneous pool of the metal in the circulation, unmanaged iron, seems to be a principal source of iron-mediated organ damage.

The toxicity associated with excess iron, whether a systemic or a focal problem, derives from its interaction with reactive oxygen species, for instance, endogenous hydrogen peroxide ($H_2O_2$) [Graf, E.; Mahoney, J. R; Bryant, R. G.; Eaton, J. W. Iron-Catalyzed Hydroxyl Radical Formation. Stringent Requirement for Free Iron Coordination Site. J. Biol. Chem. 1984, 259, 36203624; Halliwell, B. Free Radicals and Antioxidants: A Personal View. Nutr. Rev. 1994, 52, 253-265; Halliwell, B. Iron, Oxidative Damage, and Chelating Agents. In The Development of Iron Chelators for Clinical Use; Bergeron, R. J., Brittenham, G. M., Eds.; CRC: Boca Raton, 1994; pp 3356; Koppenol, W. Kinetics and Mechanism of the Fenton Reaction: Implications for Iron Toxicity. In Iron Chelators: New Development Strategies; Badman, D. G., Bergeron, R. J., Brittenham, G. M., Eds.; Saratoga: Ponte Vedra Beach, F L, 2000; pp 3-10]. In the presence of Fe(II), $H_2O_2$ is reduced to the hydroxyl radical (HO.), a very reactive species, and HO⁻, a process known as the Fenton reaction. The Fe(III) liberated can be reduced back to Fe(II) via a variety of biological reductants (e.g., ascorbate), a problematic cycle. The hydroxyl radical reacts very quickly with a variety of cellular constituents and can initiate free radicals and radical-mediated chain processes that damage DNA and membranes, as well as produce carcinogens [Halliwell, B. Free Radicals and Antioxidants: A Personal View. Nutr. Rev. 1994, 52, 253-265; Babbs, C. F. Oxygen Radicals in Ulcerative Colitis. Free Radic. Biol. Med. 1992, 13, 169-181; Hazen, S. L.; d'Avignon, A; Anderson, M. M.; Hsu, F. F.; Heinecke, J. W. Human Neutrophils Employ the Myeloperoxidase-Hydrogen Peroxide-Chloride System to Oxidize a-Amino Acids to a Family of Reactive Aldehydes. Mechanistic Studies Identifying Labile Intermediates along the Reaction Pathway. J. Biol. Chem. 1998, 273, 4997-5005]. The solution to the problem is to remove excess unmanaged iron [Bergeron, R. J.; McManis, J. S.; Weimar, W. R; Wiegand, J.; Eiler-McManis, E. Iron Chelators and Therapeutic Uses. In Burger's Medicinal Chemistry; 6th ed.; Abraham, D. A, Ed.; Wiley: New York, 2003; pp 479-561].

In the majority of patients with thalassemia major or other transfusion-dependent refractory anemias, the severity of the anemia precludes phlebotomy therapy as a means of removing toxic accumulations of iron. Treatment with a chelating agent capable of sequestering iron and permitting its excretion from the body is then the only therapeutic approach available. The iron-chelating agents now in use or under clinical evaluation [Brittenham, G. M. Iron Chelators and Iron Toxicity. Alcohol 2003, 30, 151-158] include desferrioxamine B mesylate (DFO$^a$), 1,2-dimethyl-3-hydroxypyridin-4-one (deferiprone, L1), 4-[3,5-bis(2-hydroxyphenyl)-1,2,4-triazol-1-yl]benzoic acid (deferasirox, ICL670A), and the desferrithiocin (DFT) analogue, (S)-2-(2,4-dihydroxyphenyl)-4,5-dihydro-4-methyl-4-thiazolecarboxylic acid [deferitrin, (S)-4'-(HO)-DADFT, 1; Table 1]. Subcutaneous (sc) infusion of desferrioxamine B (DFO), a hexacoordinate hydroxamate iron chelator produced by *Streptomyces pilosus* [Bickel, H., Hall, G. E., Keller-Schierlein, W., Prelog, V., Vischer, E. and Wettstein, A. Metabolic Products of Actinomycetes. XXVII. Constitutional Formula of Ferrioxamine B. Helv. Chim. Acta 1960, 43, 2129-2138], is still regarded as a credible treatment for handling transfusional iron overload [Olivieri, N. F. and Brittenham, G. M. Iron-chelating Therapy and the Treatment of Thalassemia. Blood 1997, 89, 739-761; Giardina, P. J. and Grady, R. W. Chelation Therapy in β-Thalassemia: An Optimistic Update. Semin. Hematol. 2001, 38, 360-366]. DFO is not orally active, and when administered sc, has a very short half-life in the body and must therefore be given by continuous infusion over long periods of time [Olivieri, N. F. and Brittenham, G. M. Iron-chelating Therapy and the Treatment of Thalassemia. Blood 1997, 89, 739-761; Pippard, M. J. Desferrioxamine-Induced Iron Excretion in Humans. Bailliere's Clin. Haematol. 1989, 2, 323-343]. For these reasons, patient compliance is a serious problem [Olivieri, N. F. and Brittenham, G. M. Iron-chelating Therapy and the Treatment of Thalassemia. Blood 1997, 89, 739-761; Giardina, P. J. and Grady, R. W. Chelation Therapy in β-Thalassemia: An Optimistic Update. Semin. Hematol. 2001, 38, 360-366]. The orally active bidentate chelator, deferiprone, is licensed in Europe and some other countries as second-line therapy to DFO [Hoffbrand, A V.; Al-Refaie, F.; Davis, B.; Siritanakatkul, N.; Jackson, B. F. A; Cochrane, J.; Prescott, E.; Wonke, B. Long-term Trial of Deferiprone in 51 Transfusion-Dependent Iron Overloaded Patients. Blood 1998, 91, 295-300; Olivieri, N. F. Long-term Therapy with Deferiprone. Acta Haematoi. 1996, 95, 37-48; Olivieri, N. F.; Brittenham, G. M.; McLaren, C. E.; Templeton, D. M.; Cameron, R. G.; McClelland, R. A; Burt, A D.; Fleming, K. A Long-Term Safety and Effectiveness of Iron-Chelation Therapy with Deferiprone for Thalassemia Major. N. Engi. J. Med. 1998, 339, 417-423; Richardson, D. R. The Controversial Role of Deferiprone in the Treatment of Thalassemia. J. Lab. Clin. Med. 2001, 137, 324-329]. Unfortunately, although it is orally active, it is less efficient than sc DFO at removing iron. Whereas the orally active tridentate chelator deferasirox has now been approved by the FDA, it did not demonstrate non-inferiority to DFO. Furthermore, it apparently has a somewhat narrow therapeutic window, owing to potential nephrotoxicity, noted in animals during the preclinical toxicity studies [Nisbet-Brown, E.; Olivieri, N. F.; Giardina, P. J.; Grady, R. W.; Neufeld, E. J.; Sechaud, R; Krebs-Brown, A J.; Anderson, J. R; Alberti, D.; Sizer, K. c.; Nathan, D. G. Effectiveness and Safety of ICL670 in Iron-Loaded Patients with Thalassaemia: a Randomised, Double-Blind, Placebo-Controlled, Dose-Escalation Trial. Lancet 2003, 361, 1597-1602; Galanello, R; Piga, A; Alberti, D.; Rouan, M.-C.; Bigler, H.; Sechaud, R. Safety, Tolerability, and Pharmacokinetics of ICL670, a New Orally Active lron-Chelating Agent in Patients with Transfusion-Dependent Iron Overload Due to Thalassemia. J. Clin. Pharmacol. 2003, 43, 565-572; Cappellini, M. D. Iron-chelating therapy with the new oral agent ICL670 (Exjade). Best Pract Res Clin Haematol 2005, 18, 289-298]. In addition, Novartis has recently (April, 2007) updated the prescribing information for deferasirox: "Cases of acute renal failure, some with a fatal outcome, have been reported following the postmarketing use of Exjade® (deferasirox). Most of the fatalities occurred in patients with multiple co-morbidities and who were in advanced stages of their hematological disorders" [Exjade Prescribing Information, www.pharma.us.novartis.com/product/pi/pdf/exjade.pdf (accessed May 2007)]. Finally, ligand 1 is an orally active tridentate DFT analogue now in phase I/II trials in patients. Although the preclinical toxicity profile of 1 was relatively benign, that is, no geno- or reproductive toxicity and only mild nephrotoxicity at high doses, the clinical results remain to be elucidated.

It is an object of the present invention to provide novel desferrithiocin analogues useful for the treatment of iron overload in mammals and the diseases associated therewith.

SUMMARY OF THE INVENTION

The above and other objects are realized by the present invention, one embodiment of which relates to relatively non-toxic desazadesferrithiocin analogs having the formula:

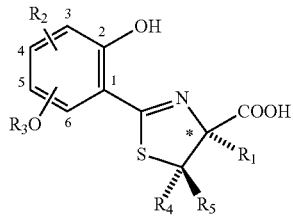

wherein: $R_1$, $R_2$, $R_4$ and $R_5$ may be the same or different and may be H, straight or branched chain alkyl having up to 14 carbon atoms, e.g., methyl, ethyl, propyl and butyl, or arylalkyl wherein the aryl portion is hydrocarbyl and the alkyl portion is straight or branched chain, the arylalkyl group having up to 14 carbon atoms, $R_2$ $R_2$ optionally being alkoxy having up to 14 carbon atoms;

$R_3$ is $[(CH_2)n-O]_x$—$[(CH_2)n-O]_y$-alkyl;

n is, independently, an integer from 1 to 8;

x is an integer from 1 to 8;

y is an integer from 0 to 8, and $R_3O$ may occupy any position on the phenyl ring except the 4-position, or a salt, hydrate or solvate thereof.

An additional embodiment of the invention relates to a method of treating a pathological condition responsive to chelation or sequestration of a trivalent metal in a subject comprising administering to the subject a therapeutically effective amount of an analog described above. In certain embodiments, the pathological condition is diabetes. In certain embodiments, the pathological condition is liver disease. In certain embodiments, the pathological condition is Friedreich ataxia (FRDA). In certain embodiments, the pathological condition is heart disease. In certain embodiments, the pathological condition is radiation injury.

A still further embodiment of the invention relates to a pharmaceutical composition for treating a pathological condition responsive to chelation or sequestration of a trivalent metal comprising an effective amount of at least one analog described above and a pharmaceutically acceptable carrier therefore.

Another embodiment of the invention relates to an article of manufacture comprising packaging material and a pharmaceutical agent contained within said packaging material, wherein said pharmaceutical agent is effective for the treatment of a subject suffering from trivalent metal overload, and wherein said packaging material comprises a label which indicates that said pharmaceutical agent can be used for ameliorating the symptoms associated with trivalent metal overload, and wherein said pharmaceutical agent is an analog described above.

There has thus been outlined, rather broadly, the more important features of the invention in order that the detailed description thereof that follows may be better understood, and in order that the present contribution to the art may be better appreciated. There are, of course, additional features of the invention that will be described further hereinafter. Indeed, it is to be understood that both the foregoing general description and the following detailed description are exemplary and explanatory and are intended to provide further explanation of the invention as claimed.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that equivalent constructions insofar as they do not depart from the spirit and scope of the present invention, are included in the present invention.

The accompanying drawings are included to provide a further understanding of the invention and are incorporated in and constitute a part of this specification, illustrate several embodiments of the invention and together with the description serve to explain the principals of the invention.

DETAILED DESCRIPTION OF THE INVENTION

Figure 1:
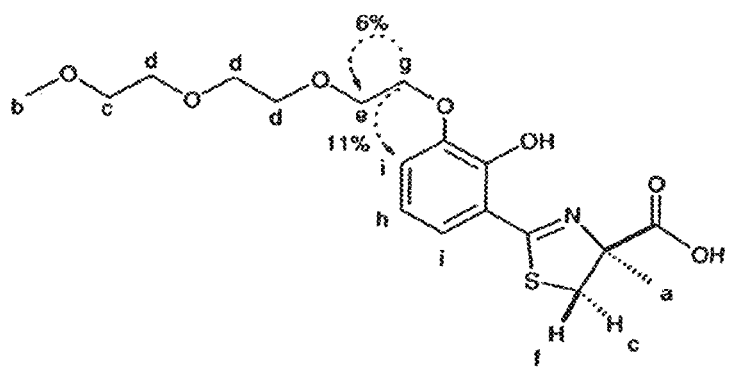
FIG. 1. $^1$H resonances and pertinent homonuclear NOE correlations for (S)-3'-(HO)-DADFT-PE (9); the percent NOE is indicated next to the dotted lines.

The present invention is predicated on the discovery that desazadesferrithiocin analogs as described above are very effective relatively non-toxic chelators of trivalent metals, particularly iron, in mammals.

More particularly, the present invention is predicated on the discovery that introducing polyether groups at various positions of the desazadesferrithiocin (DADFT) aromatic ring greatly enhances the iron clearance and organ distribution properties of the resulting analogues. Three DADFT polyethers are evaluated: (S)-4,5-dihydro-2-[2-hydroxy-4-(3,6,9-trioxadecyloxy)phenyl]-4-methyl-4-thiazolecarboxylic acid [(S)-4'-(HO)-DADFT-PE, 3], S)-4,5-dihydro-2-[2-hydroxy-5-(3,6,9-trioxadecyloxy)phenyl]-4-methyl-4-thiazolecarboxylic acid [(S)-5'-(HO)-DADFT-PE, 6], and (S)-4,5-dihydro-2-[2-hydroxy-3-(3,6,9-trioxadecyloxy)phenyl]-4-methyl-4-thiazolecarboxylic acid [(S)-3'-(HO)-DADFT-PE, 9]. The iron-clearing efficiency (ICE) in rodents and primates is shown to be very sensitive to which positional isomer is evaluated, as is the organ distribution in rodents. The polyethers had uniformly higher ICEs than their corresponding parent ligands in rodents, consistent with in vivo ligand-serum albumin binding studies. Ligand 9 is the most active polyether analogue in rodents and is also very effective in primates, suggesting a higher index of success in humans. In addition, this analogue is also shown to clear more iron in the urine of the primates than many of the other chelators. If this trend was also observed in patients, performance of iron-balance studies in a clinical setting would be much easier.

Ligand 1 is an orally active tridentate DFT analogue now in Phase VII trials in patients. Although the preclinical toxicity profile of 1 was relatively benign, i.e., no geno- or reproductive toxicity and only mild nephrotoxicity at high doses, the clinical results remain to be elucidated. Previous studies revealed that within a family of desferrithiocin analogues the more lipophilic chelators have better iron-clearing efficiency, that is, the larger the log $P_{app}$ value of the compound, the better the iron-clearing efficiency (ICE) [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783; Bergeron, R. J., Wiegand, J., McManis, J. S., Bussenius, J., Smith, R. E. and Weimar, W. R. Methoxylation of Desazadesferrithiocin Analogues: Enhanced Iron Clearing Efficiency. J. Med. Chem. 2003, 46, 1470-1477; Bergeron, R. J., Wiegand, J., McManis, J. S. and Bharti, N. The Design, Synthesis, and Evaluation of Organ-Specific Iron Chelators. J. Med. Chem. 2006, 49, 7032-7043]. There also exists a second, albeit somewhat disturbing relationship: in all sets of ligands, the more lipophilic chelator is always the more toxic [Bergeron, R. J.; Wiegand, J.; McManis, J. S.; Vinson, J. R. T.; Yao, H.; Bharti, N.; Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. A previous investigation focused on the design of ligands that balance the lipophilicity/toxicity relationship while iron-clearing efficiency is maintained. The study began with the observation that (S)-4,5-dihydro-2-(2-hydroxy-4-methoxyphenyl)-4-methyl-4-thiazolecarboxylic acid [(S)-4'-(CH$_3$O)-DADFT, 2], a 4'-methyl-ether, had excellent iron-clearing efficiency in both rodents and primates; however, it was unacceptably toxic [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783; Bergeron, R. J., Wiegand, J., McManis, J. S., Bussenius, J., Smith, R. E. and Weimar, W. R. Methoxylation of Desazadesferrithiocin Analogues: Enhanced Iron Clearing Efficiency. J. Med. Chem. 2003, 46, 1470-1477]. Nevertheless, this established that alkylation of the 4'-(HO) functionality of (S)-4'-(HO)-DADFT (1) was compatible with the iron-clearing function. On the basis of these observations, a less lipophilic, more water-soluble ligand than 2 was assembled, the polyether (S)-4,5-dihydro-2-[2-hydroxy-4-(3,6,9-trioxadecyloxy)phenyl]-4-methyl-4-thiazolecarboxylic acid [(S)-4'-(HO)-DADFT-PE, 3] [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783].

When 1 was 4'-methoxylated to provide 2, the ICE in a rodent model after oral (po) administration increased substantially from 1.1±0.8% to 6.6±2.8% (p<0.02) [Bergeron, R. J., Wiegand, J., McManis, J. S. and Bharti, N. The Design, Synthesis, and Evaluation of Organ-Specific Iron Chelators. J. Med. Chem. 2006, 49, 7032-7043]. The polyether (3), in which a 3,6,9-trioxadecyl group was fixed to the 4'-(HO) of 1, also performed well, with an ICE of 5.5±1.9% when administered po (p<0.003 vs 1) [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. The efficiency of 1 given po to iron-loaded primates was 16.8±7.2% [Bergeron, R. J., Wiegand, J., McManis, J. S. and Bharti, N. The Design, Synthesis, and Evaluation of Organ-Specific Iron Chelators. J. Med. Chem. 2006, 49, 7032-7043] while the ICE of the 4'-(CH$_3$O) analogue (2) given po was 24.4±10.8% [Bergeron, R. J., Wiegand, J., McManis, J. S., Bussenius, J., Smith, R. E. and Weimar, W. R. Methoxylation of Desazadesferrithiocin Analogues: Enhanced Iron Clearing Efficiency. J. Med. Chem. 2003, 46, 1470-1477]. The corresponding polyether (3) given po performed very well in primates with an efficiency of 25.4±7.4% [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783].

Earlier studies carried out in rodents clearly demonstrated the polyether (S)-4'-(HO)-DADFT-PE (3) to be less nephrotoxic than the corresponding (S)-4'-(CH$_3$O)-DADFT analogue (2) or the parent drug (S)-4'-(HO)-DADFT (1) [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. In an attempt to understand this difference in toxicity, the tissue levels of 3 and 1 in the liver, kidney, pancreas, and heart of rodents given a single sc 300 μmol/kg dose of the chelators were measured 2, 4, 6, and 8 h after exposure [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. There were two notable observations. At each time point, the level of the polyether 3 in the liver was much higher than that of the parent drug 1. In the kidney, the polyether concentration was lower than the parent at 2 h and similar at later time points [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. This seemed consistent with the reduced nephrotoxicity. R. Furthermore, in an experiment in which 1 and 3 were given po to the rats twice daily at a dose of 237 μmol/kg/dose (474 μmol/kg/day) for 7 days [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarbox-ylic Acid Polyethers: A Solution to Nephrotoxicity. J. Med. Chem. 2006, 49, 2772-2783], under light microscopy, the proximal tubules of kidneys from the polyether (3)-treated rodents were indistinguishable from those of the control animals; the distal tubules presented with occasional vacuolization but were otherwise normal [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. However, animals treated with 1 showed regional, moderate to severe vacuolization in the proximal tubules, a loss of the brush border, and tubular extrusions toward the lumen; the distal tubules showed moderate to severe vacuolization. These findings, coupled with the increased ICE of the polyether 3, compelled us to pursue further studies on additional polyethers and evaluate drug tissue levels at additional (earlier) time points.

Desferrithiocin, (S)-4,5-dihydro-2-(3-hydroxy-2-pyridinyl)-4-methyl-4-thiazolecarboxylic acid (DFT), is a tridentate siderophore siderophore [Naegeli, H.-D.; Zahner, H. Metabolites of Microorganisms. Part 193. Ferrithiocin. Helv. Chim. Acta 1980, 63, 1400-1406] that forms a stable 2:1 complex with Fe(III); the cumulative formation constant is $4 \times 10^{29}$ M$^{-1}$ [Hahn, F. E.; McMurry, T. J.; Hugi, A; Raymond, K. N. Coordination Chemistry of Microbial Iron Transport. 42. Structural and Spectroscopic Characterization of Diastereomeric Cr(III) and Co(III) Complexes of Desferriferrithiocin. J. Am. Chem. Soc. 1990, 112, 1854-1860; Anderegg, G.; Raber, M. Metal Complex Formation of a New Siderophore Desferrithiocin and of Three Related Ligands. J. Chern. Soc. Chern. Cornrnun. 1990, 1194-1196]. It performed well when given orally (po) in both the bile duct-cannulated rodent model (ICE, 5.5%) [Bergeron, R. J.; Wiegand, J.; Dionis, J. B.; Egli-Karmakka, M.; Frei, J.; Huxley-Tencer, A.; Peter, H. H. Evaluation of Desferrithiocin and Its Synthetic Analogues as Orally Effective Iron Chelators. J. Med. Chern. 1991, 34, 2072-2078] and in the iron-overloaded *Cebus apella* primate (ICE, 16%) [Bergeron, R. J.; Streiff, R. R; Creary, E. A; Daniels, R. D., Jr.; King, W.; Luchetta, G.; Wiegand, J.; Moerker, T.; Peter, H. H. A Comparative Study of the Iron-Clearing Properties of Desferrithiocin Analogues with DFO in a *Cebus* Monkey Model. Blood 1993, 81, 21662173; Bergeron, R. J.; Streiff, R. R; Wiegand, J.; Vinson, J. R. T.; Luchetta, G.; Evans, K. M.; Peter, H.; Jenny, H.-B. A Comparative Evaluation of Iron Clearance Models. Ann. N. Y. Acad. Sci. 1990, 612, 378-393]. Unfortunately, DFT is severely nephrotoxic [Bergeron, R. J., Streiff, R. R., Creary, E. A., Daniels, R. D., Jr., King, W., Luchetta, G., Wiegand, J., Moerker, T. and Peter, H. H. A Comparative Study of the Iron-Clearing Properties of Desferrithiocin Analogues with Desferrioxamine B in a *Cebus* Monkey Model. Blood 1993, 81, 2166-2173]. Nevertheless, the outstanding oral activity spurred a structure-activity study to identify an orally active and safe DFT analogue. The initial goal was to define the minimal structural platform compatible with iron clearance on po administration [Bergeron, R. J., Streiff, R. R., Creary, E. A., Daniels, R. D., Jr., King, W., Luchetta, G., Wiegand, J., Moerker, T. and Peter, H. H. A Comparative Study of the Iron-Clearing Properties of Desferrithiocin Analogues with Desferrioxamine B in a *Cebus* Monkey Model. Blood 1993, 81, 2166-2173]'[Bergeron, R. J., Wiegand, J., Dionis, J. B., Egli-Karmakka, M., Frei, J., Huxley-Tencer, A. and Peter, H. H. Evaluation of Desferrithiocin and Its Synthetic Analogues as Orally Effective Iron Chelators. J. Med. Chem. 1991, 34, 2072-2078]. This was followed by a series of structure-activity studies aimed at developing a DFT analogue with good oral iron-clearing activity and an acceptable toxicity profile [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783; Bergeron, R. J., Wiegand, J., McManis, J. S., McCosar, B. H., Weimar, W. R., Brittenham, G. M. and Smith, R. E. Effects of C-4 Stereochemistry and C-4' Hydroxylation on the Iron Clearing Efficiency and Toxicity of Desferrithiocin Analogues. J. Med. Chem. 1999, 42, 2432-2440]. The outcome was (S)-4'-(HO)-DADFT (1), now in clinical trials. However, animal studies suggested that even in this system, the dose-limiting toxicity would likely be nephrotoxicity [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. We next discovered that fixing a polyether to the 4'-position leading to (S)-4'-(HO)-DADFT-PE (3) profoundly reduced nephrotoxicity. The reduction in proximal tubule damage seemed consistent with the reduced level of 3 in the kidney relative to the parent ligand 1 at 2 h [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783].

Figure 4:
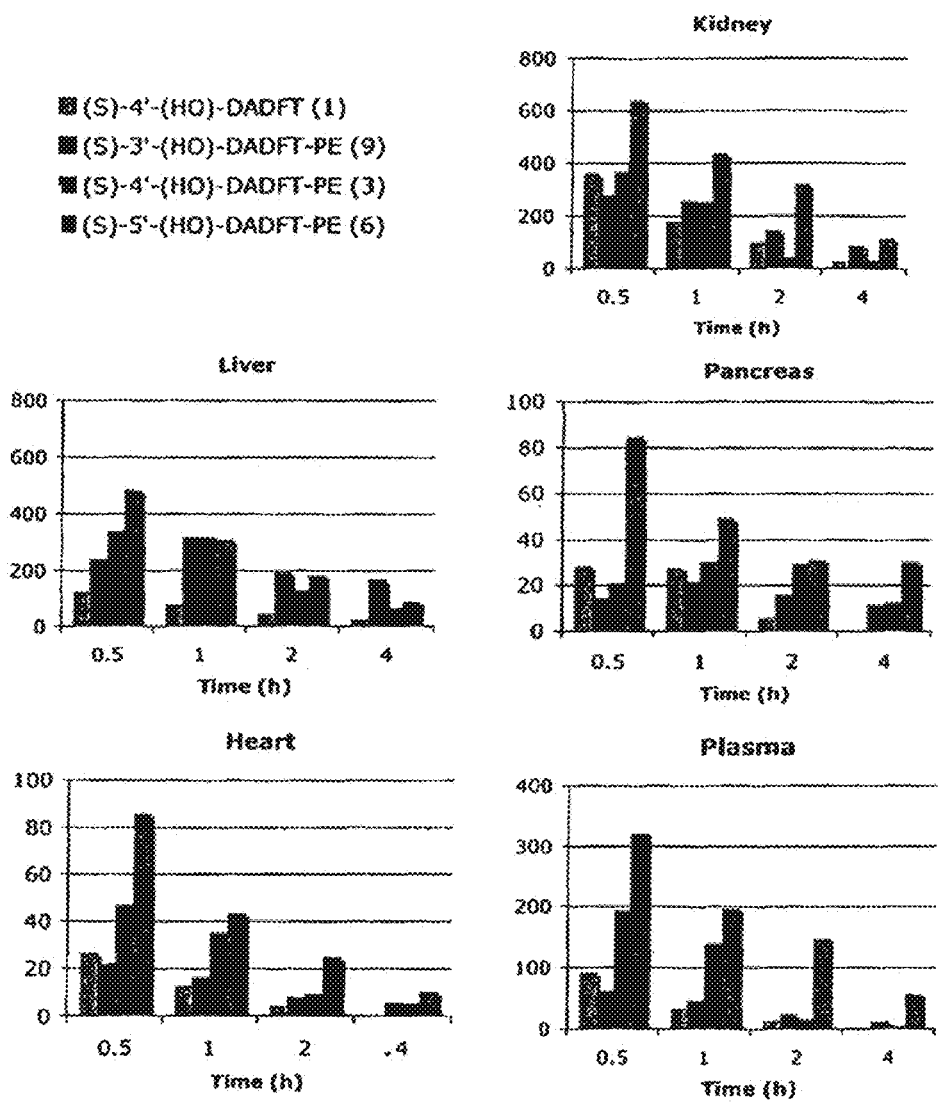
FIG. 4. Tissue distribution in plasma, kidney, liver, heart and pancreas of rats treated with DADFT analogues 1, 3, 6 and 9 given sc at a dose of 300 μmol/kg. The concentrations (y-axis) are reported as μM (plasma) or as nmol compound per g wet weight of tissue. For all time points, n=3.
Figure 5:
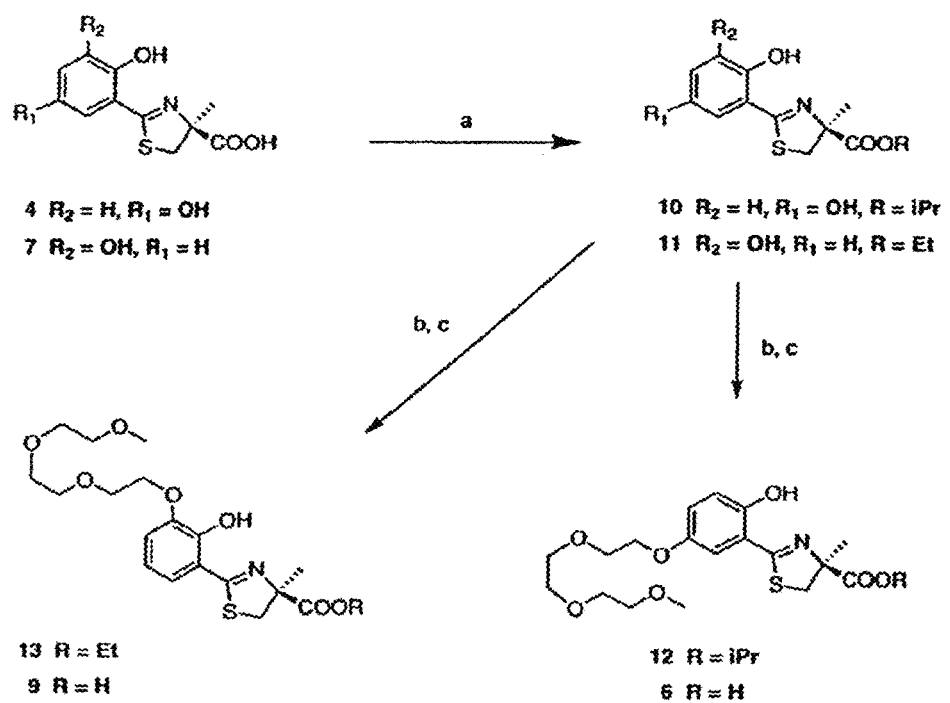
FIG. 5—Scheme 1. Synthesis of (S)-5'-(OH)-DADFT-PE (6) and (S)-3'-(OH)-DADFT-PE (9).

It was decided to better understand the role the polyether fragment plays from a positional isomer standpoint; the design strategies are based on comparative issues. Three questions are addressed: How does altering the position of the polyether in the aromatic ring affect (1) iron-clearing efficiency in rodents, (2) iron-clearing efficiency in primates, and (3) tissue distribution in rodents? With this information, we will decide how best to conduct possible further and protracted toxicity trials in rodents A platform, (S)-4,5-dihydro-2-(2-hydroxyphenyl)-4-methyl-thiazolecarboxylic acid (DADFT) is evaluated in this study. In each instance, a single substituent, hydroxy, methoxy, or 3,6,9-trioxadecyloxy was added to the 3' (7-9), 4' (1-3) or 5' (4-6) positions of the aromatic ring. In each instance, the iron-clearance data is presented in both rodents and primates, along with log $P_{app}$ numbers (Tables 1 and 2). Historical data are included [Bergeron, R. J.; Wiegand, J.; McManis, J. S.; Bharti, N. The Design, Synthesis, and Evaluation of Organ-Specific Iron Chelators. J. Med. Chem. 2006, 49, 7032-7043; Bergeron, R. J.; Wiegand, J.; McManis, J. S.; Vinson, J. R. T.; Yao, H.; Bharti, N.; Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783; Bergeron, R. J.; Wiegand, J.; McManis, J. S.; McCosar, B. H.; Weimar, W. R; Brittenham, G. M.; Smith, R. E. Effects of C-4 Stereochemistry and C-4' Hydroxylation on the Iron Clearing Efficiency and Toxicity of Desferrithiocin Analogues. J. Med. Chem. 1999, 42, 2432-2440; Bergeron, R. J.; Wiegand, J.; McManis, J. S.; Bussenius, J.; Smith, R. E.; Weimar, W. R. Methoxylation of Desazadesferrithiocin Analogues: Enhanced Iron Clearing Efficiency. J. Med. Chem. 2003, 46, 1470-1477; Bergeron, R. J.; Wiegand, J.; McManis, J. S.; Weimar, W. R; Park, J.-H.; Eiler-McManis, E.; Bergeron, J.; Brittenham, G. M. Partition-Variant Desferrithiocin Analogues: Organ Targeting and Increased Iron Clearance. J. Med. Chem. 2005, 48, 821-831]. Discussion of organ distribution of the ligands in rodents is limited to (S)-4'-(HO)-DADFT (1) and the three trioxadecyloxy compounds 3, 6 and 9 (FIG. 4). Organ distribution data for the non-polyethers 2, 4 and 5 can be found in a previous publication [Bergeron, R. J.; Wiegand, J.; McManis, J. S.; Bharti, N. The Design, Synthesis, and Evaluation of Organ-Specific Iron Chelators. J. Med. Chem. 2006, 49, 7032-7043]. Supporting Information Available: Elemental analytical data for synthesized compounds.

The syntheses of (S)-4,5-dihydro-2-[2-hydroxy-5-(3,6,9-trioxadecyloxy)phenyl]-4-methyl-4-thiazolecarboxylic acid [(S)-5'-(HO)-DADFT-PE, 6] and (S)-4,5-dihydro-2-[2-hydroxy-3-(3,6,9-trioxadecyloxy)phenyl]-4-methyl-4-thiazolecarboxylic acid [(S)-3'-(HO)-DADFT-PE (9)] were achieved by first converting (S)-2-(2,5-dihydroxyphenyl)-4,5-dihydro-4-methyl-4-thiazolecarboxylic acid [(S)-5'-(HO)-DADFT, 4] and (S)-2-(2,3-dihydroxyphenyl)-4,5-dihydro-4-methyl-4-thiazolecarboxylic acid [(S)-3'-(HO)-DADFT, 7] to their isopropyl ester 10 and ethyl ester 11, respectively (Scheme 1). (S)-5'-(HO)-DADFT (4) was converted to its isopropyl ester 10 in quantitative yield by alkylation with 2-iodopropane (1.8 equiv) in DMF in the presence of N, N-diisopropylethylamine (1.8 equiv). The ethyl ester of (S)-3'-(HO)-DADFT, 11, was accessed by alkylation of 7 with iodoethane (1.8 equiv) and N,N-diisopropylethylamine (1.8 equiv) in DMF. Compounds 10 and 11 were then alkylated at the 5'-hydroxyl and 3'-hydroxyl using an equimolar amount of tri(ethylene glycol) monomethyl ether under Mitsunobu conditions [diisopropyl azodicarboxylate (1.19 equiv) and triphenylphosphine (1.23 equiv) in THF], providing (S)-5'-(HO)-DADFT-PE-iPrE (12) and (S)-3'-(HO)-DADFT-PE-EE (13) in 52 and 25% yields, respectively. Hydrolysis of isopropyl and ethyl ester with 50% NaOH in methanol followed by acidification with 2N HCl furnished (S)-5'-(HO)-DADFT-PE (6, 97%) and (S)-3'-(HO)-DADFT-PE (9) in 60% yield.

To demonstrate that the polyether chain of 9 was indeed fixed to the 3'-position and not to its 2'-hydroxyl, proton nuclear Overhauser effect (NOE) difference spectra were acquired and the results are shown in FIG. 1. Low-power saturation of the resonance at 4.28 ppm, assigned to the protons of the polyether's methylene (g) most proximate to the aromatic residue, enhanced the signal for the adjacent methylene (e) at 3.94 ppm by 6%, while a single aromatic signal at 7.30 ppm (i) also showed a significant enhancement of 11%. These observations are consistent with the structure for 9.

Figure 2:
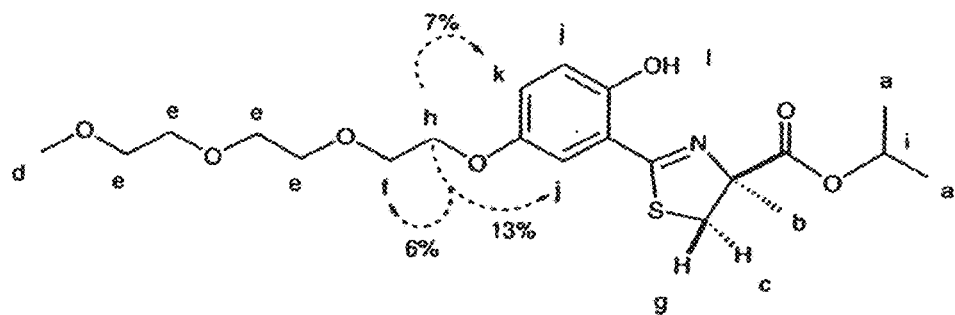
FIG. 2. $^1$H resonances and pertinent homonuclear NOE correlations for (S)-5'-(HO)-DADFT-PE-iPrE (12); the percent NOE is indicated next to the dotted lines.

Proton NOE difference spectroscopy was also used to verify that alkylation of the polyether chain occurred at the 5'-position in 12 and not at the more sterically hindered 2'-hydroxyl; these results are shown in FIG. 2. Irradiation of the signal at 4.10 ppm, assigned to methylene (h) in the polyether chain, enhanced the neighboring methylene (f) resonance at 3.84 ppm by 6%, and two aromatic signals at 6.94 ppm (j) and 7.01 ppm (k) showed significant enhancements of 13% and 7% respectively. These enhancements indicate that the structure for 12 is correct as shown and, thus, the resulting hydrolysis product is indeed 6.

Figure 3:
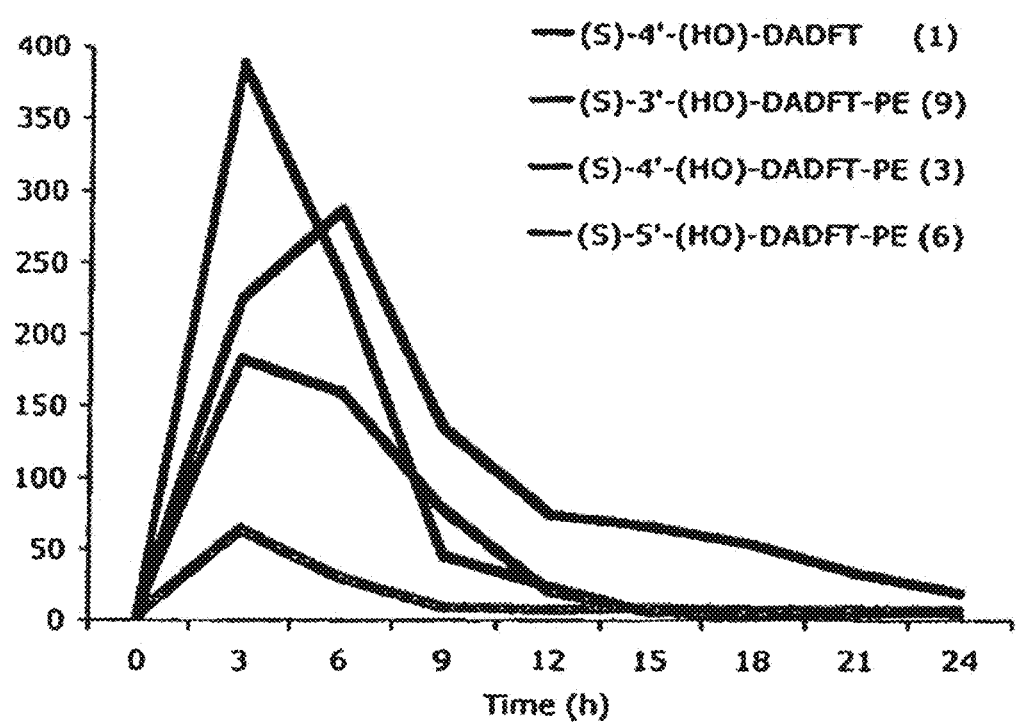
FIG. 3. Biliary ferrokinetics of rats treated with DADFT analogues 1, 3, 6 and 9 given po at a dose of 300 μmol/kg. The iron clearance (y-axis) is reported as μg of iron per kg body weight.

Chelator-Induced Iron Clearance in Non-Iron-Overloaded Rodents. We previously demonstrated that in the (S)-4'-(HO)-DADFT series, (S)-4'-(HO)-DADFT (1), (S)-4'-(CH$_3$O)-DADFT (2), and (S)-4'-(HO)-DADFT-PE (3), both the methoxy ligand (2; ICE 6.6±2.8%) and the polyether (3; ICE 5.5±1.9%) were more efficient iron chelators than the parent ligand 1; ICE 1.1±0.8% (p<0.02 vs 2 and p<0.003 vs 3), respectively (Table 1) [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. Recall that iron-clearing efficiency (ICE) is defined as (net iron excretion)/(total iron-binding capacity of the chelator), expressed as a percent. The relative ICE values of compounds 1 and 2 were in keeping with their log P$_{app}$ values: the more lipophilic, the larger log P$_{app}$, the more efficient the chelator. This was not the case with the polyether analogue 3; it was much more active than its log P$_{app}$ would have predicted. However, the ICE trend was in keeping with the biliary ferrokinetics (FIG. 3) and liver concentration of the chelators, for example, 3>1 (FIG. 4).

With the (S)-5'-(HO)-DADFT series (Table 1), (S)-5'-(HO)-DADFT (4), (S)-4,5-dihydro-2-(2-hydroxy-5-methoxyphenyl)-4-methyl-4-thiazolecarboxylic acid [(S)-5'-(CH$_3$O)-DADFT, 5], and (S)-5'-(HO)-DADFT-PE (6), both the methoxy analogue 5 (ICE 6.3±1.2%) and the polyether 6 (ICE 8.0±1.8%) were more efficient iron chelators than the parent ligand 4 (ICE 1.0±0.9%, p<0.001 vs 5 and p<0.005 vs 6, respectively). Again, the relative ICEs of 4 versus 5 were in keeping with the log P$_{app}$ and liver concentrations [Bergeron, R. J., Wiegand, J., McManis, J. S. and Bharti, N. The Design, Synthesis, and Evaluation of Organ-Specific Iron Chelators. J. Med. Chem. 2006, 49, 7032-7043]. Although liver concentration (FIG. 4) was a good indicator of the ICE of polyether 6, relative to 4 [Bergeron, R. J., Wiegand, J., McManis, J. S. and Bharti, N. The Design, Synthesis, and Evaluation of Organ-Specific Iron Chelators. J. Med. Chem. 2006, 49, 7032-7043], log P$_{app}$ was not. It is notable that in both the (S)-5'-(HO)-DADFT and the (S)-4'-(HO)-DADFT series, the corresponding HO—, CH$_3$O— and polyether ligands have similar ICE values and similar iron-clearance distribution in the urine and bile (Table 1).

The ICEs of the (S)-3'-(HO)-DADFT set of compounds 7-9 are very different than the 4'-(HO) and 5'-(HO) series. The ligands are, as a family, more efficient at clearing iron (Table 1). Again, although the relative iron-clearing efficiencies are predicted by the log P$_{app}$ values for the 3'-(HO) and 3'-(CH$_3$O) compounds, the ICE for the 3'-polyether (9) is not. What is most relevant in this instance is the profound difference in ICE between the 3'-polyether (9) and the 4'-polyether (3); the 3'-ligand (9) is nearly 200% more effective (10.6±4.4% vs 5.5±1.9%, p<0.05). The ICE of 9 is also greater than that of the 5'-polyether 6, (10.6±4.4% vs 8.0±1.8%, respectively), but the increase is slightly less than significant (p=0.06). The modes of iron excretion, urine versus bile, are similar.

The biliary ferrokinetics of the parent 1 and the three polyethers 3, 6 and 9 (FIG. 3) show that the iron clearance (µg/kg) of ligand 1 peaks at 3 h postdrug and never exceeds 68 µg/kg. The iron excretion induced by the 4'- and 5'-polyethers (3 and 6) also peak at 3 h, but at much higher levels, 183 and 388 µg/kg, respectively (p<0.001 for 1 vs 3 or 6). The biliary iron content of 3'-polyether 9 treated animals is greatest at 6 h, 287 µg/kg. In addition, while the biliary iron clearance for 1, 3 and 6 have returned to baseline levels by 15 h, the 3'-polyether (9) remains well above this until >30 h (data not shown). The delayed peak in iron excretion and duration of activity of 9 are also reflected in the tissue distribution studies (FIG. 4), discussed below.

Chelator-Induced Iron Clearance in Iron-Overloaded *Cebus apella* Primates. The iron-clearance data for all three sets of ligands are presented (Table 2). In the case of the (S)-4'-(HO)-DADFT series in primates, while the mean ICE values for (S)-4'-(HO)-DADFT (1) and (S)-4'-(CH$_3$O)-DADFT (2) suggest a correlation with log P$_{app}$, for example, the ICE of the more lipophilic analogue 2 (24.4±10.8%) [Bergeron, R. J., Wiegand, J., McManis, J. S., Bussenius, J., Smith, R. E. and Weimar, W. R. Methoxylation of Desazadesferrithiocin Analogues: Enhanced Iron Clearing Efficiency. J. Med. Chem. 2003, 46, 1470-1477]>1 (16.8±7.2%) [Bergeron, R. J., Wiegand, J., McManis, J. S., McCosar, B. H., Weimar, W. R., Brittenham, G. M. and Smith, R. E. Effects of C-4 Stereochemistry and C-4' Hydroxylation on the Iron Clearing Efficiency and Toxicity of Desferrithiocin Analogues. J. Med. Chem. 1999, 42, 2432-2440], the increase is not significant. Although (S)-4'-(HO)-DADFT-PE (3) is the least lipophilic chelator in the 1-3 series, it is just as efficient (ICE, 25.4±7.4%) [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783] as analogue 2 and is slightly more effective than the parent 1, although the increase was not quite significant (p=0.06).

In the case of the (S)-5'-(HO)-DADFT analogues 4-6, the ligands' ICE trend correlates well with log P$_{app}$. The ICE of the most lipophilic ligand 5 (18.9±2.3%) is more than twice as efficient as the least lipophilic analogue 6 (ICE 8.1±2.8%, p<0.001); 5 is also more efficient than chelator 4, ICE 12.6±3.0% (p<0.01) [Bergeron, R. J., Wiegand, J., McManis, J. S. and Bharti, N. The Design, Synthesis, and Evaluation of Organ-Specific Iron Chelators. J. Med. Chem. 2006, 49, 7032-7043]. With the (S)-3'-(HO)-DADFT analogues 7-9, while there are clear differences in log $P_{app}$, the ICEs of the three ligands are all within error of each other (Table 2).

A final, comparative note concerning the polyether ligands relates to the biliary versus urinary metal excretion. In the rodent model, the numbers are generally similar, with nearly all of the iron excreted in the bile (Table 1). This is not the case with the primates; a much larger fraction of the iron is found in the urine (Table 2). The most notable cases are (S)-5'-(HO)-DADFT-PE (6) with 56/44 feces/urine ratio and (S)-3'-(HO)-DADFT-PE (9) with 72/28 feces/urine ratio in primates. In rodents, these numbers are 98/2 and 95/5, respectively.

Iron Clearance Performance Ratio in Primates versus Rodents. The performance ratio (PR), defined as the mean $ICE_{primates}/ICE_{rodents}$, is noteworthy (Table 3). At first glance, it does not seem surprising that the ligands uniformly perform better in the iron-overloaded primates than in the non-iron-overloaded rats (Tables 1 and 2). The mean ICE for the primate group can be compared with the mean ICE of the rodent group (Table 3). Although the standard deviations for the two species are not equivalent for 1-5 and 7-9, this is not a concern because the intervals containing the means do not interact. This is not the case with the 5'-polyether (6), whose ICE is virtually identical in the two species. The largest differences in performance ratios generally unfold with the parent ligands 1, 4, and 7. However, the fact that the ratios change so profoundly within sets (i.e., 1 vs 2 and 3, 4 vs 5 and 6, and 7 vs 8 and 9) suggests that the difference in ICE in primates versus rodents is not based entirely on the fact the monkeys are iron-overloaded, while the rodents are not.

The Possible Impact of Ligand-Albumin Binding on ICE. In an attempt to understand the differences in ICE between the parent ligands 1, 4, and 7 and their analogues in the rodent model, we conducted a series of experiments focused on ligand-albumin binding. We elected to focus on a drug that is under clinical trials with Genzyme, (S)-4'-(HO)-DADFT (1). Recall the corresponding polyether (3) performed significantly better in the rodent (ICE 5.5±1.9% vs 1.1±0.8% for 3 and 1, respectively) [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. A series of comparative experiments in rats focused on displacing (S)-4'-(HO)-DADFT (1) and (S)-4'-(HO)-DADFT-PE (3) from serum albumin binding sites were carried out.

Benzoic acid has been well established as a ligand that will displace drugs from both sites in human serum albumin [Ostergaard, J., Schou, C., Larsen, C. and Heegaard, N. H. Evaluation of capillary electrophoresis-frontal analysis for the study of low molecular weight drug-human serum albumin interactions. Electrophoresis 2002, 23, 2842-2853]. We elected to evaluate the impact of treating bile duct-cannulated rodents with sodium benzoate to displace any chelator potentially bound to Sudlow types I and II albumin binding sites [Ostergaard, J., Schou, C., Larsen, C. and Heegaard, N. H. Evaluation of capillary electrophoresis-frontal analysis for the study of low molecular weight drug-human serum albumin interactions. Electrophoresis 2002, 23, 2842-2853]. Five experiments were carried out (Table 4). Rodents were given (i) sodium benzoate dissolved in distilled water at 250 mg/kg/dose sc times six doses, (ii) (S)-4'-(HO)-DADFT (1) po at 300 µmol/kg, (iii) 1 given po at 300 µmol/kg plus sodium benzoate (250 mg/kg/dose). The sodium benzoate was given 0.5 h pre-1 and hourly thereafter for five additional doses, (iv) (S)-4'-(HO)-DADFT-PE (3) administered po at 300 µmol/kg, or (v) 3 dosed at 300 µmol/kg po plus sodium benzoate (250 mg/kg/dose). The sodium benzoate was again given 0.5 h pre-3 and hourly thereafter for five additional doses. The results (Table 4) indicate that the sc administration of sodium benzoate itself does not induce the clearance of any iron. However, when sodium benzoate is administered to the rodents as described above in addition to 1, there is a 10.9-fold increase in the ICE, from 1.1±0.8% to 12.0±2.6% (p<0.001). Under the same conditions, the ICE of (S)-4'-(HO)-DADFT-PE (3) also increases, but by a much smaller magnitude, from 5.5±1.9% to 8.8±2.4% (p<0.05), a 1.6-fold increase. Lower dosing of sodium benzoate had a lesser effect on increasing the ICE of 1 (data not shown). These data are consistent with the idea that the difference in ICE in rodents between parent ligands and the corresponding polyethers may well be dependent on ligand-albumin binding differences. The data may also be consistent with the difference in performance ratios in primates versus rodents, that is, the ligands may uniformly bind less tightly to primate albumin than to rodent albumin.

Chelator Tissue Distribution in Rodents. Two issues were addressed regarding moving the 3,6,9-trioxadecyloxy (polyether) group around the DADFT aromatic ring—the impact on ICE and the effect on tissue distribution. These assessments represent the first step in identifying which, if any, additional DADFT polyethers should be moved forward into protracted toxicity trials in rodents.

The current study clearly indicates that moving the polyether from the 4'- to the 3'- or 5'-position of the aromatic ring of DADFT can have a profound effect on ICE (Tables 1 and 2) and tissue distribution (FIG. 4) of the resulting ligands. In the kidney (FIG. 4) at the 0.5 h time point, the 5'-polyether (6) achieved the highest concentration (643±92 nmol/g wet weight), followed by the 4'-polyether (3; 368±74 nmol/g wet weight, p<0.01 vs 6) and 3'-polyether (9; 280±26 nmol/g wet weight, p<0.01 vs 6). Interestingly, at this time point, the concentration of the 4'-polyether (3) and the parent (1; 361±56 nmol/g wet weight) were nearly identical (p>0.05). At 1 h, again the 5'-ligand (6) was most concentrated (435±111 nmol/g wet weight), with the 3'-chelator (9) and 4'-chelator (3) achieving very similar levels (259±35 and 252±10 nmol/g wet weight, respectively). The parent drug 1 was the least concentrated (179±4 nmol/g wet weight). At 2 h, the relative kidney levels are indeed different. Again, the 5'-ligand (6) was most concentrated (321±20 nmol/g wet weight)>>9; 145±27 nmol/g wet weight>>3; 41±3 nmol/g wet weight (p<0.001 for 6 vs 9 or 3). At 4 h, the order was now 6 (116±65 nmol/g wet weight)≈9 (90±7 nmol/g wet weight)>3 (34±13 nmol/g wet weight)≈1 (27±7 nmol/g wet weight). Recall that previous studies demonstrated the 4'-polyether (3) to be much less nephrotoxic than the parent drug (S)-4'-(HO)-DADFT (1) [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. This was consistent with the relative tissue levels at the 2 h time point: the 4'-polyether concentration 3 was much lower than the parent 1 [Bergeron, R. J., Wiegand, J., McManis, J. S., Vinson, J. R. T., Yao, H., Bharti, N. and Rocca, J. R. (S)-4,5-Dihydro-2-

(2-hydroxy-4-hydroxyphenyl)-4-methyl-4-thiazolecarboxylic Acid Polyethers: A Solution to Nephrotoxicity. J. Med. Chem. 2006, 49, 2772-2783] However, renal concentration data derived from time points taken earlier than 2 h are not consistent with the idea that reduced nephrotoxicity of the 4'-polyether (3) relative to the parent (1) can be explained simply by lower kidney chelator levels.

At 0.5 h, the liver concentrations of the three polyether ligands (FIG. 4) follow the same relative order as seen in the kidney, 6 (483±85 nmol/g wet weight)>3 (339±35 nmol/g wet weight)>9 (242±38 nmol/g wet weight). At 1 h the concentrations of all three polyether analogues are similar in the liver ($\approx$315 nmol/g wet weight). Interestingly, at 1 h, the concentration of the 3'-polyether (9) has significantly increased from 242±38 nmol/g wet weight to 318±46 nmol/g wet weight (p<0.05), while the concentrations of 6 and 3 have decreased by 36% and 6%, respectively. At 2 and 4 h, the 3'-ligand (9) is the most concentrated in the liver, followed by the 5'-analogue (6) and 4'-analogue (3). The liver concentration of the parent 1 is lower than the polyethers at all time points (FIG. 4).

In the heart at 0.5 h (FIG. 4) the relative concentration of the polyethers (6>3>9) follows the same trend as in the kidney and liver at the same time point. However, the actual levels are much lower, <90 nmol/g wet weight. The order of concentration in the heart remains the same at 1 and 2 h. At 4 h, the 5'-ligand (6) is still the most concentrated chelator. Although the parent drug 1 is higher than 9 at 0.5 h, it is the least concentrated ligand at all other time points (FIG. 4).

In the pancreas (FIG. 4), the relative concentration of the polyethers is 6>3>9 at all time points. The tissue content of both 3 and 9 increase from 0.5 to 1 h (FIG. 4). At 2 h, the levels of 3 and 6 are similar ($\approx$30 nmol/g wet weight), while the concentration of 9 is 16 nmol/g wet weight. The parent drug (1) is higher in concentration than 3 and 9 at 0.5 h and similar at 1 h (FIG. 4). At 2 h, 1 is the least concentrated ligand and is undetectable at 4 h.

The plasma chelator concentration data (FIG. 4) are consistent with the idea that the ligands are cleared quickly. At 0.5 h the plasma ligand levels [6 (324±20 µM)>3 (194±60 µM)>9 (62±24 µM)] mirror what is occurring in the liver, kidney, pancreas, and heart. At 1 h, while the order is the same, 6 has diminished by 39%, 3 has diminished by 28%, and 9 has diminished by 26%. At 2 h, 6 is now down by 54%, 3 is down by 92%, and 9 is down by 61%. At 4 h, 6 has dropped by 82%, 3 has dropped by 97% and 9 has dropped by 79%. The drop in plasma concentration of ligand 3 is considerably faster than the disappearance of 6 or 9. However, 9 never achieves plasma levels close to 3 and 6. The parent drug 1 is only higher in concentration than 9 at 0.5 h; it is lower than all other ligands at all other time points (FIG. 4). This observation relative to liver concentrations of the chelators suggests an efficient first-pass clearance of 1 and 9. Because of the excellent ICE of the 3'-polyether (9) and its moderate kidney concentrations, this ligand will be moved forward into preclinical toxicity trials. What is particularly intriguing about this ligand is the fact that it performs so well in both the rodents and the primates, suggesting a higher index of success in humans.

Early studies clearly demonstrated the polyether (S)-4'-(HO)-DADFT-PE (3) to be profoundly less nephrotoxic in rodents than the corresponding (S)-4'-(CH$_3$O)-DADFT (2) or the parent drug (S)-4'-(HO)-DADFT (1) [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. The polyether 3 was also shown to have excellent iron-clearing efficiency in primates. The histopathology of kidneys of rats treated with (S)-4'-(HO)-DADFT-PE (3) presented with significantly fewer structural alterations in the proximal tubules than did tissues taken from rodents exposed to the parent ligand 1 [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. Initial kidney tissue level measurements taken at 2 h from animals treated with the 4'-polyether (3) seemed consistent with the histopathology; there was less polyether in the kidney than the parent drug and less nephrotoxicity [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. The ICE in both rodents and primates and the absence of toxicity seen with the 4'-polyether (3) compelled the investigation of the impact of fixing the 3,6,9-polyether chain to the aromatic ring of DADFT at positions other than the 4'-carbon had on ICE and ligand tissue distribution. Two systems were chosen, (S)-3'-(HO)-DADFT-PE (9) and (S)-5'-(HO)-DADFT-PE (6) (Tables 1 and 2).

The key step in the assembly of the two ligands (Scheme 1) involved alkylation of either 2,5-dihydroxy isopropyl ester (10) or the 2,3-dihydroxy ethyl ester (11) with tri(ethylene glycol) monomethyl ether under Mitsunobu conditions. This alkylation was followed by ester hydrolysis. Mitsunobu alkylation was highly specific for the 5' or the 3' and did not involve the 2'-(HO), probably for steric reasons. The regioselectivity of the reaction was consistent with nuclear Overhauser effect difference spectra (FIGS. 1 and 2) of both polyethers 9 and 12.

While log P$_{app}$ was a predictor of ICE in the rodents in the case of the methoxylated analogues versus their corresponding parents (1 vs 2), (4 vs 5), and (7 vs 8) and with the 5'-substituted ligands 4-6 in primates, it was not a useful tool for parent versus polyether. In each set of compounds in rodents, the ICE of the polyether was significantly greater than that of the parent ligand (1 vs 3, 500%, p<0.003; 4 vs 6, 800%, p<0.005 and 7 vs 9, 230%, p<0.05; Table 1). This suggested that there may well be additional parameters beyond ligand-metal access that control ICE: efficiency of the metal complex transport through various organic anion transports, such as cMOAT, log P$_{app}$ of the metal complexes themselves, and ligand-albumin binding. The ICE differences between parent and polyether, for example, (S)-4'-(HO)-DADFT (1) and (S)-4'-(HO)-DADFT-PE (3), in rodents was shown to parallel ligand-albumin binding differences (Table 3). Rodents were given sodium benzoate, a compound known to displace ligands from Sudlow types I and II albumin binding sites, along with either 1 or 3. The sc administration of sodium benzoate increased the ICE of 1 by 10.9-fold (p<0.001). The ICE of animals given ligand 3 and sodium benzoate also increased, but only by 1.6-fold (p<0.05). This may ultimately explain, at least in part, the difference in ligand ICE in primates versus rodents. The chelators may uniformly bind more weakly to primate albumin. In the primates, the differences in ligand ICE were not as profound and were generally within experimental error (Table 2), except for 4 versus 6, in which the parent's ICE (12.6±3.0%) was greater than that of the corresponding polyether 6 (8.1±2.8%, p<0.05).

The effect of altering the position of the polyether on ligand-tissue concentrations is significant (FIG. 4). The trend in all tissue concentrations except the liver is generally (S)-5'-(HO)-DADFT-PE (6)>(S)-4'-(HO)-DADFT-PE (3)>(S)-3'-(HO)-DADFT-PE (9). In the liver at 0.5 h, the concentrations are also 6>3>9>1, and at 1 h, 6≈3≈9>>1. However, beyond that time point, 9 achieves and remains at the highest concentration. The most confounding piece of data is associated with the kidney ligand concentration of (S)-4'-(HO)-DADFT-PE (3) at time points earlier than 2 h. Previous studies clearly demonstrated the 4'-polyether (3) to be much less nephrotoxic than the parent drug (S)-4'-(HO)-DADFT (1) [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. This was consistent with the renal tissue levels (1>3) at the 2 h time point [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. However, in the current study 1 and 3 were found to have similar concentrations at 0.5 h; ligand 3 is actually slightly higher than 1 at 1 h. Thus it seems that the reduced toxicity of the polyether 3 relative to the parent 1 cannot be explained simply by kidney chelator concentrations.

Finally, the performance ratios ($ICE_{primates}/ICE_{rodents}$) of ligands 3, 6 and 9 (Table 3) are all <4.6, suggesting comparable iron clearance between the two species. Although ligand 6 has virtually identical ICEs in the primates and rodents (PR=1.0), it is the least efficient (ICE 8.1±2.8%) of the three polyethers in primates and will not be pursued further. While 3'-($CH_3O$)-DADFT (8) is the most effective chelator in rodents (12.4±3.5%) and performs well in primates (22.5±7.1%), it is expected to have a toxicity profile (nephrotoxicity) similar to that of the 4'- and 5'-($CH_3O$)-DADFT ligands 2 [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783] and 5 [Bergeron, R. J., Wiegand, J., McManis, J. S. and Bharti, N. The Design, Synthesis, and Evaluation of Organ-Specific Iron Chelators. J. Med. Chem. 2006, 49, 7032-7043], respectively, and will not be moved forward. The (S)-3'-(HO)-DADFT-PE (9) works well in both primates (24.5±7.6%) and rats (10.6±4.4%), PR 2.3, suggesting a higher index of success in a third species, humans. In addition, if the relatively large fraction of the iron excreted in the urine of the monkeys were also found in the urine of patients, performance of iron-balance studies would be facilitated. This chelator will be moved forward into protracted preclinical toxicological assessments in rodents.

In the Examples: *C. apella* monkeys were obtained from World Wide Primates (Miami, Fla.). Male Sprague-Dawley rats were procured from Harlan Sprague-Dawley (Indianapolis, Ind.). Cremophor RH-40 was acquired from BASF (Parsippany, N.J.). Ultrapure salts were purchased from Johnson Matthey Electronics (Royston, U.K.). All hematological and biochemical studies [Bergeron, R. J., Streiff, R. R., Creary, E. A., Daniels, R. D., Jr., King, W., Luchetta, G., Wiegand, J., Moerker, T. and Peter, H. H. A Comparative Study of the Iron-Clearing Properties of Desferrithiocin Analogues with Desferrioxamine B in a *Cebus* Monkey Model. Blood 1993, 81, 2166-2173] were performed by Antech Diagnostics (Tampa, Fla.). Atomic absorption (AA) measurements were made on a Perkin-Elmer model 5100 PC (Norwalk, Conn.). Histopathological analysis was carried out by Florida Vet Path (Bushnell, Fla.).

Cannulation of Bile Duct in Non-Iron-Overloaded Rats has been described previously. The cannulation has been described previously. Bile samples were collected from male Sprague-Dawley rats (400-450 g) at 3-h intervals for up to 48 h. The urine sample(s) was taken at 24 h intervals. Sample collection and handling are as previously described [Bergeron, R. J., Streiff, R. R., Creary, E. A., Daniels, R. D., Jr., King, W., Luchetta, G., Wiegand, J., Moerker, T. and Peter, H. H. A Comparative Study of the Iron-Clearing Properties of Desferrithiocin Analogues with Desferrioxamine B in a *Cebus* Monkey Model. Blood 1993, 81, 2166-2173; Bergeron, R. J., Streiff, R. R., Wiegand, J., Vinson, J. R. T., Luchetta, G., Evans, K. M., Peter, H. and Jenny, H.-B. A Comparative Evaluation of Iron Clearance Models. Ann. N. Y. Acad. Sci. 1990, 612, 378-393].

The monkeys (3.5-4 kg) were iron overloaded with intravenous iron dextran as specified in earlier publications to provide about 500 mg of iron per kg of body weight [Bergeron, R. J., Streiff, R. R., Wiegand, J., Luchetta, G., Creary, E. A. and Peter, H. H. A Comparison of the Iron-Clearing Properties of 1,2-Dimethyl-3-hydroxypyrid-4-one, 1,2-Diethyl-3-hydroxypyrid-4-one, and Deferoxamine. Blood 1992, 79, 1882-1890]; the serum transferrin iron saturation rose to between 70 and 80%. At least 20 half-lives, 60 d [Wood, J. K., Milner, P. F. and Pathak, U. N. The Metabolism of Iron-dextran Given as a Total-dose Infusion to Iron Deficient Jamaican Subjects. Br. J. Haematol. 1968, 14, 119-129], elapsed before any of the animals were used in experiments evaluating iron-chelating agents.

Fecal and urine samples were collected at 24-h intervals and processed as described previously [Bergeron, R. J., Streiff, R. R., Creary, E. A., Daniels, R. D., Jr., King, W., Luchetta, G., Wiegand, J., Moerker, T. and Peter, H. H. A Comparative Study of the Iron-Clearing Properties of Desferrithiocin Analogues with Desferrioxamine B in a *Cebus* Monkey Model. Blood 1993, 81, 2166-2173; Bergeron, R. J., Streiff, R. R., Wiegand, J., Vinson, J. R. T., Luchetta, G., Evans, K. M., Peter, H. and Jenny, H.-B. A Comparative Evaluation of Iron Clearance Models. Ann. N. Y. Acad. Sci. 1990, 612, 378-393; Bergeron, R. J., Wiegand, J. and Brittenham, G. M. HBED: A Potential Alternative to Deferoxamine for Iron-Chelating Therapy. Blood 1998, 91, 1446-1452]. Briefly, the collections began 4 d prior to the administration of the test drug and continued for an additional 5 d after the drug was given. Iron concentrations were determined by flame atomic absorption spectroscopy as presented in other publications [Bergeron, R. J., Streiff, R. R., Wiegand, J., Vinson, J. R. T., Luchetta, G., Evans, K. M., Peter, H. and Jenny, H.-B. A Comparative Evaluation of Iron Clearance Models. Ann. N. Y. Acad. Sci. 1990, 612, 378-393; Bergeron, R. J., Wiegand, J., Wollenweber, M., McManis, J. S., Algee, S. E. and Ratliff-Thompson, K. Synthesis and Biological Evaluation of Naphthyldesferrithiocin Iron Chelators. J. Med. Chem. 1996, 39, 1575-1581].

In the iron-clearing experiments, the rats were given a single 300 µmol/kg dose of drugs 1-9 orally (po). The compounds were administered as (1) a solution in water (3) or (2) the monosodium salt of the compound of interest (prepared by the addition of 1 equiv of NaOH to a suspension of the free acid in distilled water (1-2, 4-9). The drugs were given to the monkeys po at a dose of 75 µmol/kg (6, 9) or 150 µmol/kg (1-5, 7-8). The drugs were prepared as for the rats, except that 2 and 7-8 were solubilized in 40% Cremophor RH-40/water.

The theoretical iron outputs of the chelators were generated on the basis of a 2:1 complex. The efficiencies in the rats and monkeys were calculated as set forth elsewhere [Bergeron, R. J., Wiegand, J., McManis, J. S., McCosar, B. H., Weimar, W. R., Brittenham, G. M. and Smith, R. E. Effects of C-4 Stereochemistry and C-4' Hydroxylation on the Iron Clearing Efficiency and Toxicity of Desferrithiocin Analogues. J. Med. Chem. 1999, 42, 2432-2440]. Data are presented as the mean±the standard error of the mean; p-values were generated via a one-tailed student's t-test, in which the inequality of variances was assumed; and a p-value of <0.05 was considered significant.

Collection of Tissue Distribution Samples from Rodents: Male Sprague-Dawley rats (250-350 g) were given a single sc injection of the monosodium salts of 6 and 9 prepared as described above at a dose of 300 µmol/kg. At times 0.5, 1, 2, and 4 h after dosing (n=3 rats per time point) the animals were euthanized by exposure to $CO_2$ gas. Blood was obtained via cardiac puncture into vacutainers containing sodium citrate. The blood was centrifuged, and the plasma was separated for analysis. The liver, heart, kidneys, and pancreas were then removed from the animals. Tissue samples of animals treated with (S)-4'-(HO)-DADFT (1) and (S)-4'-(HO)-DADFT-PE (3) were prepared for HPLC analysis as previously described [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783]. In the current study, tissues from the (S)-3'-(HO)-DADFT-PE (9) and (S)-5'-(HO)-DADFT-PE (6) treated rats were prepared for HPLC analysis by homogenizing them in 0.5 N $HClO_4$ at a ratio of 1:3 (w/v). Then, as a rinse, $CH_3OH$ at a ratio of 1:3 (w/v) was added and the mixture was stored at −20° C. for 30 min. This homogenate was centrifuged. The supernatant was diluted with mobile phase A (95% buffer [25 mM $KH_2PO_4$, pH 3.0]/5% $CH_3CN$), vortexed, and filtered with a 0.2 µm membrane. Analytical separation was performed on a Discovery RP Amide $C_{16}$ HPLC system with UV detection at 310 nm as described previously [Bergeron, R. J., Wiegand, J., Weimar, W. R., McManis, J. S., Smith, R. E. and Abboud, K. A. Iron Chelation Promoted by Desazadesferrithiocin Analogues: An Enantioselective Barrier. Chirality 2003, 15, 593-599; Bergeron, R. J., Wiegand, J., Ratliff-Thompson, K. and Weimar, W. R. The Origin of the Differences in (R)- and (S)-Desmethyldesferrithiocin: Iron-Clearing Properties. Ann. N. Y. Acad. Sci. 1998, 850, 202-216]. Mobile phase and chromatographic conditions were as follows: solvent A, 5% $CH_3CN$/95% buffer; solvent B, 60% $CH_3CN$/40% buffer. The concentrations were calculated from the peak area fitted to calibration curves by nonweighted least-squares linear regression with Rainin Dynamax HPLC Method Manager software (Rainin Instrument Co.). The method had a detection limit of 0.25 µM and was reproducible and linear over a range of 1-1000 µM.

Tissue distribution data are presented as the mean; p-values were generated via a one-tailed student's t-test, in which the inequality of variances was assumed and a p-value of <0.05 was considered significant.

Compounds 4 and 7 were synthesized using the method published earlier [Bergeron, R. J., Wiegand, J., McManis, J. S. and Bharti, N. The Design, Synthesis, and Evaluation of Organ-Specific Iron Chelators. J. Med. Chem. 2006, 49, 7032-7043; Bergeron, R. J., Wiegand, J., McManis, J. S., Weimar, W. R., Park, J.-H., Eiler-McManis, E., Bergeron, J. and Brittenham, G. M. Partition-Variant Desferrithiocin Analogues: Organ Targeting and Increased Iron Clearance. J. Med. Chem. 2005, 48, 821-831]. Reagents were purchased from Aldrich Chemical Co. (Milwaukee, Wis.), and Fisher Optima grade solvents were routinely used. DMF was distilled under inert atmosphere and THF was distilled from sodium and benzophenone. Reactions were run under a nitrogen atmosphere, and organic extracts were dried with sodium sulfate and filtered. Silica gel 40-63 from SiliCycle, Inc. was used for flash column chromatography. C-18 for reverse phase column chromatography was obtained from Sigma Chemical Co. Optical rotations were run at 589 nm (sodium D line) utilizing a Perkin-Elmer 341 polarimeter, with c being the concentration in grams of compound per 100 mL of solution in chloroform. $^1H$ NMR spectra were recorded at 400 MHz and chemical shifts (δ) are given in parts per million downfield from tetramethylsilane for $CDCl_3$ (not indicated) or sodium 3-(trimethylsilyl) propionate-2, 2, 3, 3-$d_4$ for $D_2O$. $^{13}C$ spectra were run at 100 MHz and chemical shifts (δ) are given in parts per million referenced to the residual solvent resonance in $CDCl_3$ (δ 77.16). Coupling constants (J) are in hertz, and the base peaks are reported for the ESI-FTICR mass spectra. Elemental analyses were performed by Atlantic Microlabs (Norcross, Ga.). NOE difference spectra were obtained at 500 MHz and samples were not degassed, were not spun, and the probe temperature was regulated at 27° C. For 12 the concentration was 15 mg/0.6 mL in $CDCl_3$, and for 9 the concentration was 5 mg/mL $D_2O$.

Separate spectra to investigate nuclear Overhauser effects (NOEs) were acquired by low-power irradiation off-resonance and then on the resonance for the methylene hydrogens, using a 3-second presaturation period, a 45° pulse, and a 3-second acquisition time. Typically, 100-300 acquisitions were accumulated for each pair of free induction decays before processing with exponential line broadening and Fourier transformation.

NOE difference spectra were presented by subtracting the spectrum with irradiation off-resonance from the spectrum with on-resonance presaturation. These difference spectra were then analyzed by integration of the relevant signals. The inverted methylene resonances for the two hydrogens labeled g (FIG. 1) and h (FIG. 2) were assigned an integral value of −200%, and the integrals for the positive signal enhancements of the various other resonances were then taken as percent enhancements of their parent signals. Results are reported as the average enhancements from three or four replicates of each difference spectrum.

Example 1

Isopropyl 2-(2,5-Dihydroxyphenyl)-4,5-dihydro-4-methyl-4-thiazolecarboxylate (10)

2-Iodopropane (8.95 g, 52.65 mmol) and DIEA (6.79 g, 52.65 mmol) were successively added to 4 (7.40 g, 29.25 mmol) in DMF (90 mL), and the solution was stirred at rt for 72 h. After solvent removal under hivac, the residue was treated with 1:1, 0.5 M citric acid/saturated NaCl (300 mL) and was extracted with EtOAc (250 mL, 2×100 mL). Combined organic extracts were washed with 50 mL portions of 1% $NaHSO_3$, $H_2O$, and saturated NaCl, and the solution was evaporated. Purification by flash column chromatography using 20% EtOAc in toluene generated 7.94 g of 10 (92%) as a yellow oil: $[α]^{20}$ +41.1°; $^1H$ NMR δ 1.27 and 1.29 (2 d, 6H, J=5.5), 1.65 (s, 3H), 3.21 (d, 1H, J=11.6), 3.85 (d, 1H, J=11.2), 5.09 (septet, 1H, J=6.4), 6.89 (m, 2H,); $^{13}$C NMR δ 21.70, 24.36, 40.05, 70.02, 83.78, 115.90, 115.94, 118.05, 121.59, 148.02, 153.11, 171.24, 172.57; HRMS m/z calcd for $C_{14}H_{18}NO_4S$, 296.0956 (M+H); found, 296.0956. Anal. ($C_{14}H_{17}NO_4S$) C, H, N.

Example 2

Ethyl 2-(2,3-Dihydroxyphenyl)-4,5-dihydro-4-methyl-4-thiazolecarboxylate (11)

Iodoethane (8.61 g, 55.20 mmol) and DIEA (7.13 g, 55.20 mmol) were successively added to 7 (7.36 g, 29.06 mmol) in DMF (100 mL), and the solution was stirred at rt for 48 h. After solvent removal under hivac, the residue was treated with 1:1, 0.5 M citric acid/saturated NaCl (300 mL) and was extracted with EtOAc (200 mL, 2×100 mL). Combined organic layers were washed with 150 mL portions of 1% $NaHSO_3$, $H_2O$, and saturated NaCl, and the solvent was evaporated. Purification by flash column chromatography using 10% EtOAc in DCM gave 8.01 g of 11 (98%) as a yellow oil: $[α]^{20}$ +57.41°; $^1$H NMR δδ1.31 (t, 3H, J=7.2), 1.68 (s, 3H), 3.25 (d, 1H, J=11.6), 3.88 (d, 1H, J=11.2), 4.26 (q, 2H, J=7.2), 5.71 (br s, 1H), 6.79 (t, 1H, J=7.8), 6.97 (dd, 1H, J=8.4, 1.2), 7.03 (dd, 1H, J=7.8, 1.2); $^{13}$C NMR δ 14.22, 24.56, 40.19, 62.17, 83.26, 115.74, 117.88, 119.13, 121.20, 145.11, 146.83, 172.09, 172.69; HRMS m/z calcd for $C_{13}H_{15}NO_4SNa$, 304.0619 (M+Na); found, 304.0625. Anal. ($C_{13}H_{15}NO_4S$) C, H, N.

Example 3

Isopropyl (S)-4,5-Dihydro-2-[2-hydroxy-5-(3,6,9-trioxadecyloxy)phenyl]-4-methyl-4-thiazolecarboxylate (12)

Tri(ethylene glycol) monomethyl ether (3.19 g, 19.40 mmol) and diisopropylazodicarboxylate (4.73 g, 23.39 mmol) were successively added to a solution of 10 (5.62 g, 19.02 mmol) and triphenylphosphine (5.93 g, 22.63 mmol) in dry THF (120 mL) with ice bath cooling. The solution was stirred at room temperature for 5 h and was maintained at 5° C. for 16 h. Solvent was removed by rotary evaporation, and 40% EtOAc/petroleum ether (100 mL) was added. The solution was kept at 5° C. for 12 h; the solid formed was filtered. The filtrate was concentrated in vacuo and was purified by column chromatography (50% EtOAc/petroleum ether) to give 4.36 g of 12 (52%) as a yellow oil: $[α]^{20}$ +23.2°; $^1$H NMR δδ 1.27 and 1.29 (2d, 6H, J=6.2), 1.65 (s, 3H), 3.22 (d, 1H, J=11.2), 3.53-3.58 (m, 2H), 3.64-3.71 (m, 4H), 3.72-3.77 (m, 2H), 3.84 (t, 2H, J=4.7), 3.87 (d, 1H, J=11.4), 4.08-4.12 (m, 2H), 5.08 (septet, 1H, J=4.0), 6.91-6.96 (m, 2H), 7.01 (dd, 1H, J=9.2, 3.2), 12.02 (br s, 1H); $^{13}$C NMR δ 21.71, 24.37, 40.01, 59.15, 68.52, 69.69, 69.91, 70.68, 70.76, 70.92, 72.03, 83.83, 115.23, 115.82, 118.03, 121.49, 151.17, 153.80, 171.12, 172.13; HRMS m/z calcd for $C_{21}H_{32}NO_7S$, 442.1899 (M+H); found, 442.1887. Anal. ($C_{21}H_{31}NO_7S$) C, H, N.

Example 4

(S)-4,5-Dihydro-2-[2-hydroxy-5-(3,6,9-trioxadecyloxy)phenyl]-4-methyl-4-thiazolecarboxylic Acid (6)

A solution of 50% (w/w) NaOH (3.34 mL, 94 mmol) in $CH_3OH$ (34 mL) was added to 12 (2.14 g, 4.85 mmol) in $CH_3OH$ (70 mL) with ice bath cooling. The reaction mixture was stirred at room temperature for 18 h, and the bulk of the solvent was removed by rotary evaporation. The residue was treated with dilute NaCl (100 mL) and was extracted with ether (3×50 mL). The basic aqueous phase was cooled in ice, acidified with 2 N HCl to pH=2, and extracted with EtOAc (3×100 mL). After the EtOAc layers were washed with saturated NaCl (100 mL), glassware that was presoaked in 3 N HCl for 15 min was employed henceforth. After solvent removal by rotary evaporation, 1.88 g of 6 (97%) was obtained as an orange oil: $[α]^{20}$ +40.0°; $^1$H NMR ($D_2O$) δ 1.72 (s, 3H), 3.26 (d, 1H, J=11.2), 3.38 (s, 3H), 3.54-3.58 (m, 2H), 3.64-3.71 (m, 4H), 3.72-3.76 (m, 2H), 4.07-4.11 (m, 3H), 6.91-6.95 (m, 2H), 7.01 (dd, 1H, J=9.0, 3.0); $^{13}$C NMR 624.46, 40.04, 59.04, 68.40, 69.86, 70.48, 70.62, 70.80, 71.91, 83.44, 115.21, 115.65, 118.09, 121.63, 151.12, 153.69, 171.83, 176.18; HRMS m/z calcd for $C_{18}H_{26}NO_7S$, 400.1429 (M+H); found, 400.1416.

Example 5

Ethyl (S)-4,5-Dihydro-2-[2-hydroxy-3-(3,6,9-trioxadecyloxy)phenyl]-4-methyl-4-thiazolecarboxylate (13)

Tri(ethylene glycol) monomethyl ether (1.70 g, 10.36 mmol) and diisopropylazodicarboxylate (2.53 g, 12.50 mmol) were successively added to a solution of 11 (3.0 g, 10.16 mmol) and triphenylphosphine (3.17 g, 12.09 mmol) in dry THF (60 mL) with ice bath cooling. The solution was stirred at room temperature for 8 h and was maintained at 5° C. for 40 h. Solvent was removed by rotary evaporation, and 40% EtOAc/petroleum ether (50 mL) was added. The solution was kept at 5° C. for 12 h; the solid formed was filtered. The filtrate was concentrated in vacuo and was purified by column chromatography eluting with 50% EtOAc/petroleum ether to give 1.08 g of 13 (25%) as an orange oil. An analytical sample was purified on C-18 reverse phase column eluting with equal volumes of 50% aq. MeOH and 40% aq. MeOH, respectively: $[α]^{20}$ +40.0°; $^1$H NMR δδ1.30 (t, 3H, J=7.2), 1.66 (s, 3H), 3.23 (d, 1H, J=11.2), 3.38 (s, 3H), 3.52-3.58 (m, 2H), 3.63-3.71 (m, 4H), 3.74-3.79 (m, 2H), 3.88 (d, 1H, J=11.6), 3.91 (t, 2H, J=5.0), 4.20-4.26 (m, 4H), 6.79 (t, 1H, J=7.6), 7.01-7.07 (m, 2H); $^{13}$C NMR δ 14.18, 24.47, 39.96, 59.10, 62.07, 68.95, 69.79, 70.60, 70.70, 70.91, 71.99, 83.48, 116.42, 117.62, 118.29, 122.71, 147.72, 150.35, 171.70, 172.69; HRMS m/z calcd for $C_{20}H_{29}NO_7SNa$, 450.1562 (M+Na); found, 450.1568. Anal. ($C_{20}H_{29}NO_7S$) C, H, N.

Example 6

(S)-4,5-Dihydro-2-[2-hydroxy-3-(3,6,9-trioxadecyloxy)phenyl]-4-methyl-4-thiazolecarboxylic Acid (9)

A solution of 50% (w/w) NaOH (13.88 mL, 266.02 mmol) in $CH_3OH$ (120 mL) was added to 13 (8.89 g, 20.80 mmol) in $CH_3OH$ (280 mL) with ice bath cooling. The reaction mixture was stirred at room temperature for 6 h, and the bulk of the solvent was removed by rotary evaporation. The residue was treated with dilute NaCl (300 mL) and the basic aqueous phase was cooled in ice, acidified with 2 N HCl to pH=2, and extracted with EtOAc (4×150 mL). After the EtOAc layers were washed with saturated NaCl (300 mL), glassware that was presoaked in 3 N HCl for 15 min was employed henceforth. After solvent removal by rotary evaporation, purification was done on C-18 reverse phase column, eluting with 50% aq. methanol and lyophilized to furnish 4.98 g of 9 (60%) as an orange oil: $[\alpha]^{20}$ +61.9°; $^1$H NMR (D$_2$O) δ 1.77 (s, 3H), 3.35 (s, 3H), 3.56-3.62 (m, 3H), 3.64-3.73 (m, 4H), 3.75-3.89 (m, 2H), 3.92-3.96 (m, 2H), 3.99 (d, 1H, J=11.6), 4.25-4.31 (m, 2H), 6.99 (t, 1H, J=8.2), 7.26-7.33 (m, 2H); $^{13}$C NMR δ 24.52, 39.93, 59.07, 69.04, 69.83, 70.49, 70.64, 70.86, 71.97, 83.21, 116.33, 117.94, 118.50, 122.80, 147.67, 150.24, 172.38, 176.10; HRMS m/z calcd for C$_{18}$H$_{26}$NO$_7$S, 400.1429 (M+H); found, 400.1413.

TABLE 1

Iron-Clearing Activity of Desferrithiocin Analogues When Administered Orally to Rodents and the Partition Coefficients of the Compounds

| Desferrithiocin Analogue | Iron-Clearing Efficiency (%)[a] | log P$_{app}$[b] |
|---|---|---|
| 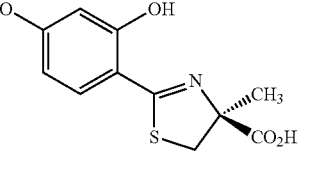 (S)-4'-(HO)-DADFT, 1 | 1.1 ± 0.8[c] [100/0] | −1.05 |
| 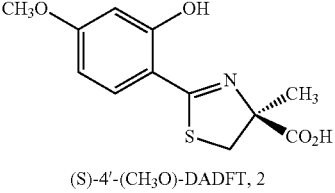 (S)-4'-(CH$_3$O)-DADFT, 2 | 6.6 ± 2.8[c] [98/2] | −0.70 |
|  (S)-4'-(HO)-DADFT-PE, 3 | 5.5 ± 1.9[c] [90/10] | −1.10 |
| 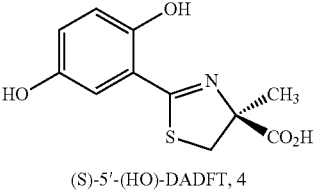 [SMILES: C[C@]1(C(=O)O)CSC(c2cc(O)ccc2O)=N1] (S)-5'-(HO)-DADFT, 4 | 1.0 ± 0.9[d] [99/1] | −1.14 |
| 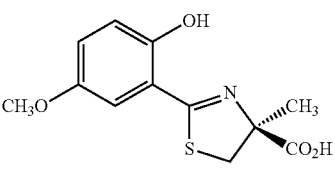 (S)-5'-(CH$_3$O)-DADFT, 5 | 6.3 ± 1.2[d] [95/5] | −0.61 |
| 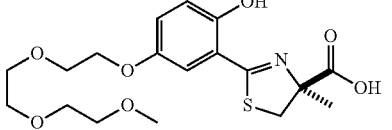 (S)-5'-(HO)-DADFT-PE, 6 | 8.0 ± 1.8 [98/2] | −1.27 |
| 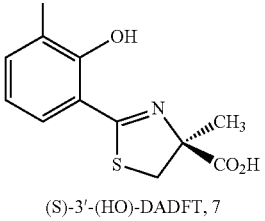 (S)-3'-(HO)-DADFT, 7 | 4.6 ± 0.9 [98/2] | −1.17 |
| 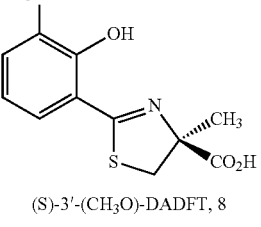 (S)-3'-(CH$_3$O)-DADFT, 8 | 12.4 ± 3.5[e] [99/1] | −1.12 |
| 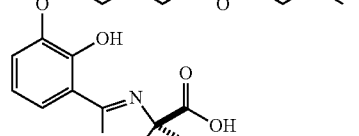 (S)-3'-(HO)-DADFT-PE, 9 | 10.6 ± 4.4[e] [95/5] | −1.22 | a. In the rodents [n=3 (6), 4 (2, 4, 5, 7, 9), 5 (3, 8), or 8 (1)], the dose was 300 μmol/kg. The compounds were solubilized in either distilled water (3) or were given as their monosodium salts, prepared by the addition of 1 equiv of NaOH to a suspension of the free acid in distilled water (1, 2, 4-9). The efficiency of each compound was calculated by subtracting the iron excretion of control animals from the iron excretion of the treated animals. This number was then divided by the theoretical output; the result is expressed as a percent. The relative percentages of the iron excreted in the bile and urine are in brackets.

b. Data are expressed as the log of the fraction in the octanol layer (log P$_{app}$); measurements were done in TRIS buffer, pH 7.4, using a "shake flask" direct method. The values obtained for compounds 1 and 2 are from Bergeron et al, *J. Med. Chem.* 2003, 46, 1470-1477; the value for 3 is from Bergeron et al, *J. Med. Chem.* 2006, 49, 2772-2783; the values for 4 and 5 are from Bergeron et al, *J. Med. Chem.* 2006, 49, 7032-7043; and the values for 7 and 8 are from Bergeron et al, *J. Med. Chem.* 2005, 48, 821-831.

c. Data are from ref Bergeron et al, *J. Med. Chem.* 2006, 49, 2772-2783.

d. Data are from ref Bergeron et al, *J. Med. Chem.* 2006, 49, 7032-7043.

e. ICE is based on a 48 h sample collection period.

TABLE 2

Iron-Clearing Activity of Desferrithiocin Analogues When Administered Orally to *Cebus apella* Primates and the Partition Coefficients of the Compounds

| Desferrithiocin Analogue | Iron-Clearing Efficiency (%)[a] | log $P_{app}$[b] |
|---|---|---|
| 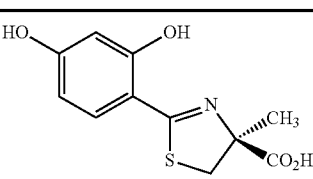 (S)-4'-(HO)-DADFT, 1 | 16.8 ± 7.2[c] [88/12] | −1.05 |
|  (S)-4'-(CH$_3$O)-DADFT, 2 | 24.4 ± 10.8[d] [91/9] | −0.70 |
| 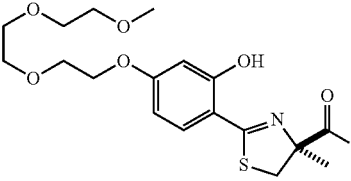 (S)-4'-(HO)-DADFT-PE, 3 | 25.4 ± 7.4[e] [96/4] | −1.10 |
| 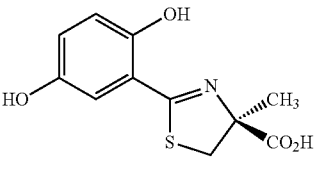 [SMILES: C[C@]1(C(=O)O)CSC(c2cc(O)ccc2O)=N1] (S)-5'-(HO)-DADFT, 4 | 12.6 ± 3.0[f] [88/12] | −1.14 |
| 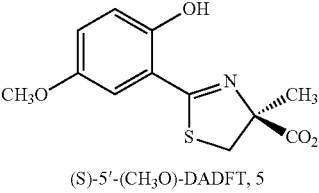 (S)-5'-(CH$_3$O)-DADFT, 5 | 18.9 ± 2.3[f] [94/6] | −0.61 |
| 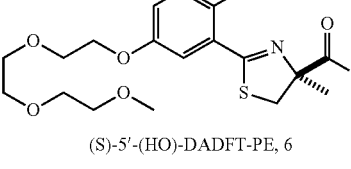 (S)-5'-(HO)-DADFT-PE, 6 | 8.1 ± 2.8[g] [56/44] | −1.27 |
| 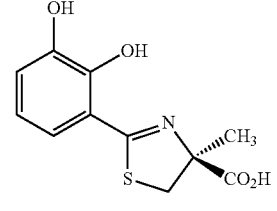 [SMILES: C[C@]1(C(=O)O)CSC(c2cccc(O)c2O)=N1] (S)-3'-(HO)-DADFT, 7 | 23.1 ± 5.9[h] [83/17] | −1.17 |
| 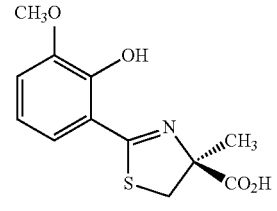 (S)-3'-(CH$_3$O)-DADFT, 8 | 22.5 ± 7.1[h] [91/9] | −1.12 |
| 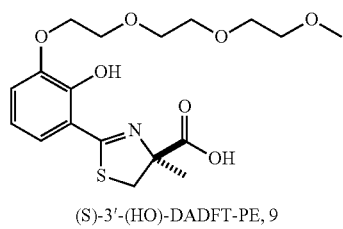 (S)-3'-(HO)-DADFT-PE, 9 | 24.5 ± 7.6[g] [72/28] | −1.22 | a. In the monkeys [n=4 (3-7), 5 (8), 6 (1), or 7 (2, 9)]. The drugs were given po at a dose of 75 μmol/kg (6, 9) or 150 μmol/kg (1-5, 7-8). The compounds were solubilized in either distilled water (3), 40% Cremophor (2, 7, 8), or were given as their monosodium salts, prepared by the addition of 1 equiv of NaOH to a suspension of the free acid in distilled water (1, 4-6, 9). The efficiency of each compound was calculated by averaging the iron output for 4 days before the administration of the drug, subtracting these numbers from the two-day iron clearance after the administration of the drug, and then dividing by the theoretical output; the result is expressed as a percent. The relative percentages of the iron excreted in the stool and urine are in brackets.

b. Data are expressed as the log of the fraction in the octanol layer (log $P_{app}$); measurements were done in TRIS buffer, pH 7.4, using a "shake flask" direct method. The values obtained for compounds 1 and 2 are from ref Bergeron et al, *J. Med. Chem.* 2003, 46, 1470-1477; the value for 3 is from ref Bergeron et al, *J. Med. Chem.* 2006, 49, 2772-2783; the values for 4 and 5 are from ref [Bergeron, R. J., Wiegand, J., McManis, J. S. and Bharti, N. The Design, Synthesis, and Evaluation of Organ-Specific Iron Chelators. J. Med. Chem. 2006, 49, 7032-7043]; the values for 7 and 8 are from Bergeron et al, *J. Med. Chem.* 2005, 48, 821-831.

c. Data are from Bergeron et al, *J. Med. Chem.* 1999, 42, 2432-2440.

d. Data are from Bergeron et al, *J. Med. Chem.* 2003, 46, 1470-1477.

e. Data are from Bergeron et al, *J. Med. Chem.* 2006, 49, 2772-2783.

f. Data are from Bergeron et al, *J. Med. Chem.* 2006, 49, 7032-7043.

g. The dose was 75 µmol/kg.

h. Data are from Bergeron et al, *J. Med. Chem.* 2005, 48, 821-831.

TABLE 3

Iron-Clearing Efficiency Performance Ratios of Desferrithiocin Analogues in Primates versus Rodents

| Desferrithiocin Analogue | ICE Primate/ICE Rodent |
|---|---|
| (S)-4'-(HO)-DADFT, 1 | 15.3 |
| (S)-4'-(CH₃O)-DADFT, 2 | 3.7 |
| (S)-4'-(HO)-DADFT-PE, 3 | 4.6 |
| (S)-5'-(HO)-DADFT, 4 | 12.6 |
| (S)-5'-(CH₃O)-DADFT, 5 | 3.0 |
| (S)-5'-(HO)-DADFT-PE, 6 | 1.0 |
| (S)-3'-(HO)-DADFT, 7 | 5.0 |
| (S)-3'-(CH₃O)-DADFT, 8 | 1.8 |
| (S)-3'-(HO)-DADFT-PE, 9 | 2.3 |

TABLE 4

Ligand-Albumin Binding in Rodents treated with Sodium Benzoate[a]

| experiment | dose | route | N | iron-clearing efficiency (%) |
|---|---|---|---|---|
| sodium benzoate | 250 mg/kg/dose | sc | 5 | baseline iron excretion |
| (S)-4'-(HO)-DADFT (1) | 300 µmol/kg | po | 8 | 1.1 ± 0.8 |
| (S)-4'-(HO)-DADFT (1) plus sodium benzoate | 300 µmol/kg and 250 mg/kg/dose, respectively | po and sc, respectively | 5 | 12.0 ± 2.6[b] |
| (S)-4'-(HO)-DADFT-PE (3) | 300 µmol/kg | po | 5 | 5.5 ± 1.9 |
| (S)-4'-(HO)-DADFT-PE (3) plus sodium benzoate | 300 µmol/kg and 250 mg/kg/dose, respectively | po and sc, respectively | 4 | 8.8 ± 2.4[c] | a. Ligand 1 was administered po as its monosodium salt, prepared by the addition of 1 equiv of NaOH to a suspension of the free acid in distilled water. Ligand 3 was dissolved in distilled water and given po. Sodium benzoate was dissolved in distilled water and given sc at 250 mg/kg/dose×6 doses. The first dose of sodium benzoate was given 0.5 h prior to the chelators; additional doses were given hourly thereafter for the next 5 h.

b. p<0.001 vs non-benzoate 1 treated animals.

c. p<0.05 vs non-benzoate 3 treated animals.

The invention also includes enantiomers and mixtures of enantiomers (e.g., racemic mixtures) of the compounds represented by the above formulas along with their salts (e.g., pharmaceutically acceptable salts), solvates and hydrates. Compounds of the invention can exist in optically active forms that have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that one or more chiral carbons are non-superimposable mirror images of one another. A specific stereoisomer, which is an exact minor image of another stereoisomer, can also be referred to as an enantiomer, and a mixture of such isomers is often called an enantiomeric mixture. A 50:50 mixture of enantiomers is referred to as a racemic mixture.

Many of the compounds described herein can have one or more chiral centers and therefore can exist in different enantiomeric forms. If desired, a chiral carbon can be designated with an asterisk (*). In the present application, the chiral carbon at the 4-position of the thiazoline or thiazolidine ring can be designated with an asterisk, because the configuration of this carbon is of particular interest. When bonds to chiral carbons are depicted as straight lines in the formulas of the invention, it is understood that both the (R) and (S) configurations of each chiral carbon, and hence both enantiomers and mixtures thereof, are embraced within the formula. As is used in the art, when it is desired to specify the absolute configuration about a chiral carbon, a bond to the chiral carbon can be depicted as a wedge (bonds to atoms above the plane) and another can be depicted as a series or wedge of short parallel lines (bonds to atoms below the plane). The Cahn-Ingold-Prelog system can be used to assign the (R) or (S) configuration to a chiral carbon. A chiral carbon at the 4-position of a thiazoline or thiazolidine ring preferably has an (S) configuration.

When compounds of the present invention contain one chiral center, compounds not prepared by an asymmetric synthesis exist in two enantiomeric forms and the present invention includes either or both enantiomers and mixtures of enantiomers, such as the specific 50:50 mixture referred to as a racemic mixture. The enantiomers can be resolved by methods known to those skilled in the art, for example, by formation of diastereoisomeric salts that may be separated, for example, by crystallization (See, CRC Handbook of Optical Resolutions via Diastereomeric Salt Formation by David Kozma (CRC Press, 2001)); formation of diastereoisomeric derivatives or complexes that may be separated, for example, by crystallization, gas-liquid or liquid chromatography; selective reaction of one enantiomer with an enantiomer-specific reagent, for example, enzymatic esterification; or gas-liquid or liquid chromatography in a chiral environment, for example, on a chiral support (e.g., silica with a bound chiral ligand) or in the presence of a chiral solvent. It will be appreciated that where the desired enantiomer is converted into another chemical entity by one of the separation procedures described above, a further step is required to liberate the desired enantiomeric form.

Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or, in other words, is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50% in an enantiomeric mixture. For example, when a mixture contains 80% of a first enantiomer and 20% of a second enantiomer, the enantiomeric excess of the first enantiomer is 60%. In the present invention, the enantiomeric excess can be about 20% or more, particularly about 40% or more, more particularly about 60% or more, such as about 70% or more, for example about 80% or more, such as about 90% or more. In a particular embodiment when a specific absolute configuration is designated, the enantiomeric excess of depicted compounds is at least about 90%. In a more particular embodiment, the enantiomeric excess of the compounds is at least about 95%, such as at least about 97.5%, for example, at least about 99% enantiomeric excess. When a compound of the present invention has two or more chiral carbons where R4 and R5 are not the same, it can have more than two optical isomers and can exist in diastereomeric forms. For example, when there are two chiral carbons, the compound can have up to 4 optical isomers and 2 pairs of enantiomers ((S,S)/(R,R) and (R,S)/(S,R>>. The pairs of enantiomers (e.g., (S,S)/(R,R>> are mirror image stereoisomers of one another. The stereo isomers which are not minor-images (e.g., (S,S) and (R,S>> are diastereomers. The diastereomeric pairs may be separated by methods known to those skilled in the art, for example, chromatography or crystallization and the individual enantiomers within each pair may be separated as described above. The present invention includes each diastereomer of such compounds and mixtures thereof.

An alkyl group is a saturated hydrocarbon in a molecule that is bonded to one other group in the molecule through a single covalent bond from one of its carbon atoms. Alkyl groups can be cyclic or acyclic, branched or unbranched (straight chained). An alkyl group typically has from 1 to about 14 carbon atoms, for example, one to about six carbon atoms or one to about four carbon atoms. Lower alkyl groups have one to four carbon atoms and include methyl, ethyl, n-propyl, iso-propyl, n-butyl, see-butyl and tert-butyl.

When cyclic, an alkyl group typically contains from about 3 to about 10 carbons, for example, from about 3 to about 8 carbon atoms, e.g., a cyclopropyl group, a cyclobutyl group, a cyclopentyl group, a cyclohexyl group, a cycloheptyl group or a cyclooctyl group.

Aryl groups include carbocyclic aromatic groups such as phenyl, p-tolyl, 1-naphthyl, 2-naphthyl, 1-anthracyl and 2-anthracyl. Aryl groups also include heteroaromatic groups such as N-imidazolyl, 2-imidazolyl, 2-thienyl, 3-thienyl, 2furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aryl groups also include fused polycyclic aromatic ring systems in which a carbocyclic, alicyclic, or aromatic ring or heteroaryl ring is fused to one or more other heteroaryl or aryl rings. Examples include 2-benzothienyl, 3-benzothienyl, 2benzofuranyl, 3-benzofuranyl, 2-indolyl, 3-indolyl, 2-quinolinyl, 3-quinolinyl, 2-benzothiazolyl, 2-benzoxazolyl, 2-benzimidazolyl, 1-isoquinolinyl, 3-isoquinolinyl, 1-isoindolyl and 3-isoindolyl.

Also included in the present invention are salts and pharmaceutically acceptable salts of the compounds described herein. Compounds disclosed herein that possess a sufficiently acidic functional group, a sufficiently basic functional group or both, can react with a number of organic or inorganic bases, and inorganic and organic acids, to form salts. Acidic groups can form salts with one or more of the metals listed above, along with alkali and alkaline earth metals (e.g., sodium, potassium, magnesium, calcium). In addition, acidic groups can form salts with amines. Compounds of the invention can be supplied as a transition, lanthanide, actinide or main group metal salt. For example, the salt can be a Ga (III) salt of a compound. As a transition, lanthanide, actinide or main group metal salt, compounds of the invention tend to form a complex with the metal. For example, if a compound of the invention is tridentate and the metal it forms a salt with has six coordinate sites, then a 2 to 1 compound to metal complex is formed. The ratio of compound to metal will vary according to the denticity of the metal and the number of coordination sites on the metal (preferably each coordination site is filled by a compound of the invention, although a coordination site can be filled with other anions such as hydroxide, halide or a carboxylate).

Alternatively, the compound can be a substantially metal-free (e.g. iron-free) salt. Metal-free salts are not typically intended to encompass alkali and alkali earth metal salts. Metal-free salts are advantageously administered to a subject suffering from, for example, a metal overload condition or to an individual suffering from toxic metal exposure or from focal concentrations of metals causing untoward effects.

Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the hydroxide, sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-I-sulfonate, naphthalene-2sulfonate, mandelate, and the like.

The compounds disclosed herein can be prepared in the form of their hydrates, such as hemihydrate, monohydrate, dihydrate, trihydrate, tetrahydrate and the like and as solvates.

Subjects suffering from a pathological condition responsive to chelation or sequestration of a trivalent metal can be treated with a therapeutically or prophylactically effective amount of a compound or pharmaceutical compound of the invention. One particular type of pathological condition that is responsive to chelation of a trivalent metal is a trivalent metal overload condition (e.g., an iron overload condition, an aluminum overload condition, a chromium overload condition). Another type of pathological condition that is responsive to metal chelation or sequestration is when the amount of free trivalent metal is elevated (e.g., in the serum or in a cell), such as when there is insufficient storage capacity for trivalent metals or an abnormality in the metal storage system that leads to metal release.

Iron overload conditions or diseases can be characterized by global iron overload or focal iron overload. Global iron overload conditions generally involve an excess of iron in multiple tissues or excess iron located throughout an organism. Global iron overload conditions can result from excess uptake of iron by a subject, excess storage and/or retention of iron, from, for example, dietary iron or blood transfusions. One global iron overload condition is primary hemochromatosis, which is typically a genetic disorder. A second global iron overload condition is secondary hemochromatosis, which is typically the result of receiving multiple (chronic) blood transfusions. Blood transfusions are often required for subjects suffering from thalassemia or sickle cell anemia. A type of dietary iron overload is referred to as Bantu siderosis, which is associated with the ingestion of home-brewed beer with high iron content.

In focal iron overload conditions, the excess iron is limited to one or a few cell types or tissues or a particular organ. Alternatively, symptoms associated with the excess iron are limited to a discrete organ, such as the heart, lungs, liver, pancreas, kidneys or brain. It is believed that focal iron overload can lead to neurological or neurodegenerative disorders such as Parkinson's disease, Alzheimer's disease, Huntington's disease, neuroferritinopathy, amyotrophic lateral sclerosis and multiple sclerosis. Pathological conditions that benefit from metal chelation or sequestration are often associated with deposition of the metal in the tissues of a subject. Deposition can occur globally or focally, as described above.

A subject in need of oxidative stress reduction can have one or more of the following conditions: decreased levels of reducing agents, increased levels of reactive oxygen species, mutations in or decreased levels of antioxidant enzymes (e.g., Cu/Zn superoxide dismutase, Mn superoxide dismutase, glutathione reductase, glutathione peroxidase, thioredoxin, thioredoxin peroxidase, DT-diaphorase), mutations in or decreased levels of metal-binding proteins (e.g., transferrin, ferritin, ceruloplasmin, albumin, metallothionein), mutated or overactive enzymes capable of producing superoxide (e.g., nitric oxide synthase, NADPH oxidases, xanthine oxidase, NADH oxidase, aldehyde oxidase, dihydroorotate dehydrogenase, cytochrome c oxidase), and radiation injury. Increased or decreased levels of reducing agents, reactive oxygen species, and proteins are determined relative to the amount of such substances typically found in healthy persons.

A subject in need of oxidation stress reduction can be suffering from an ischemic episode. Ischemic episodes can occur when there is mechanical obstruction of the blood supply, such as from arterial narrowing or disruption. Myocardial ischemia, which can give rise to angina pectoris and myocardial infarctions, results from inadequate circulation of blood to the myocardium, usually due to coronary artery disease. Ischemic episodes in the brain that resolve within 24 hours are referred to as transient ischemic attacks. A longer-lasting ischemic episode, a stroke, involves irreversible brain damage, where the type and severity of symptoms depend on the location and extent of brain tissue whose access to blood circulation has been compromised. A subject at risk of suffering from an ischemic episode typically suffers from atherosclerosis, other disorders of the blood vessels, increased tendency of blood to clot, or heart disease. The compounds of this invention can be used to treat these disorders.

A subject in need of oxidation stress reduction can be suffering from inflammation. Inflammation is a fundamental pathologic process consisting of a complex of cytologic and chemical reactions that occur in blood vessels and adjacent tissues in response to an injury or abnormal stimulation caused by a physical, chemical, or biologic agent. Inflammatory disorders are characterized inflammation that lasts for an extended period (i.e., chronic inflammation) or that damages tissue. Such inflammatory disorders can affect a wide variety of tissues, such as respiratory tract, joints, bowels, and soft tissue. The compounds of this invention can be used to treat these disorders.

Although not bound by theory, it is believed that the compounds of the invention derive their ability to reduce oxidative stress through various mechanisms. In one mechanism, the compound binds to a metal, particularly a redox-active metal (e.g., iron), and fills all of the coordination sites of the metal. When all of the metal coordination sites are filled, it is believed that oxidation and/or reducing agents have a diminished ability to interact with the metal and cause redox cycling. In another mechanism, the compound stabilizes the metal in a particular oxidation state, such that it is less likely to undergo redox cycling. In yet another mechanism, the compound itself has antioxidant activity (e.g., free radical scavenging, scavenging of reactive oxygen or nitrogen species). Desferrithiocin and its derivatives and analogues are known to have intrinsic antioxidant activity, as described in U.S. Application Publication No. 2004/0044220, published Mar. 4, 2004, and U.S. Application Publication No. 2004/0132789, published Jul. 8, 2004 and PCT Application No. WO2004/017959, published Mar. 4, 2004, US Application Publication No. 2003/0236417, published Dec. 25, 2003, and U.S. Pat. Nos. 6,083,966, 6,559,315, 6,525,080, 6,521,652 the contents of each of which are incorporated herein by reference.

It has also been reported that the reduction of iron overloads in humans can aid in the prevention of or control of the growth of cancer [Ozaki, et al, JAMA, Feb. 14, 2007-Vol. 297, No. 6, pp 603-610; Kalinowski et al, "The evolution of iron chelators for the treatment of iron overload disease and cancer", Pharmacological Reviews, vol 57, 4 pgs 547-83 (2005); Taetle et al, "Combination Iron Depletion Therapy", J. Nat. Cancer Inst., 81, 1229-1235 (1989); Bergeron et al, "Influence of Iron on in vivo Proliferation and Lethality of L1210 Cells", J. Nutr., 115, 369-374 (1985)]. Indeed, Ozaki et al report that the hypothesis that accumulated iron contributes to disease risk through iron-catalyzed free radical-mediated damage to critical biomolecules and through altered cellular function rests on secure biochemical grounds. However, they also report that the relationship between iron and disease has remained essentially hidden because of inconsistent findings. Finally Osaki et al report data that support findings of a pronounced "all-cause mortality decrease" associated with iron levels reduced to normal levels in humans.

A "subject" is typically a human, but can also be an animal in need of treatment, e.g., companion animals (e.g., dogs, cats, and the like), farm animals (e.g., cows, pigs, horses, sheep, goats and the like) and laboratory animals (e.g., rats, mice, guinea pigs, non-human primates and the like).

The compounds and pharmaceutical compositions of the present invention can be administered by an appropriate route. Suitable routes of administration include, but are not limited to, orally, intraperitoneally, subcutaneously, intramuscularly, transdermally, rectally, sub lingually, intravenously, buccally or via inhalation. Preferably, compounds and pharmaceutical compositions of the invention are administered orally.

The pharmaceutical compositions of the invention preferably contain a pharmaceutically acceptable carrier or diluent suitable for rendering the compound or mixture administrable orally, parenterally, intravenously, intradermally, intramuscularly or subcutaneously, rectally, via inhalation or via buccal administration, or transdermally.

The active ingredients may be admixed or compounded with a conventional, pharmaceutically acceptable carrier or diluent. It will be understood by those skilled in the art that a mode of administration, vehicle or carrier conventionally employed and which is inert with respect to the active agent may be utilized for preparing and administering the pharmaceutical compositions of the present invention. Illustrative of such methods, vehicles and carriers are those described, for example, in Remington's Pharmaceutical Sciences, 18th ed. (1990), the disclosure of which is incorporated herein by reference.

The formulations of the present invention for use in a subject comprise the agent, together with one or more acceptable carriers or diluents therefore and optionally other therapeutic ingredients. The carriers or diluents must be "acceptable" in the sense of being compatible with the other ingredients of the formulation and not deleterious to the recipient thereof. The formulations can conveniently be presented in unit dosage form and can be prepared by any of the methods well known in the art of pharmacy. All methods include the step of bringing into association the agent with the carrier or diluent which constitutes one or more accessory ingredients. In general, the formulations are prepared by uniformly and intimately bringing into association the agent with the carriers and then, if necessary, dividing the product into unit dosages thereof.

Forms suitable for oral administration include tablets, troches, capsules, elixirs, suspensions, syrups, wafers, chewing gum or the like prepared by art recognized procedures. The amount of active compound in such therapeutically useful compositions or preparations is such that a suitable dosage will be obtained.

A syrup formulation will generally consist of a suspension or solution of the compound or salt in a liquid carrier, for example, ethanol, glycerine or water, with a flavoring or coloring agent. Where the composition is in the form of a tablet, one or more pharmaceutical carriers routinely used for preparing solid formulations can be employed. Examples of such carriers include magnesium stearate, starch, lactose and sucrose. Where the composition is in the form of a capsule, the use of routine encapsulation is generally suitable, for example, using the aforementioned carriers in a hard gelatin capsule shell. Where the composition is in the form of a soft gelatin shell capsule, pharmaceutical carriers routinely used for preparing dispersions or suspensions can be considered, for example, aqueous gums, celluloses, silicates or oils, and are incorporated in a soft gelatin capsule shell.

Formulations suitable for parenteral administration conveniently include sterile aqueous preparations of the agents that are preferably isotonic with the blood of the recipient. Suitable carrier solutions include phosphate buffered saline, saline, water, lactated ringers or dextrose (5% in water).

Such formulations can be conveniently prepared by admixing the agent with water to produce a solution or suspension, which is filled into a sterile container and sealed against bacterial contamination. Preferably, sterile materials are used under aseptic manufacturing conditions to avoid the need for terminal sterilization.

Such formulations can optionally contain one or more additional ingredients, which can include preservatives such as methyl hydroxybenzoate, chlorocresol, metacresol, phenol and benzalkonium chloride. Such materials are of special value when the formulations are presented in multidose containers.

Buffers can also be included to provide a suitable pH value for the formulation.

Suitable buffer materials include sodium phosphate and acetate. Sodium chloride or glycerin can be used to render a formulation isotonic with the blood.

If desired, a formulation can be filled into containers under an inert atmosphere such as nitrogen and can be conveniently presented in unit dose or multi-dose form, for example, in a sealed ampoule.

Those skilled in the art will be aware that the amounts of the various components of the compositions of the invention to be administered in accordance with the method of the invention to a subject will depend upon those factors noted above.

A typical suppository formulation includes the compound or a pharmaceutically acceptable salt thereof which is active when administered in this way, with a binding and/or lubricating agent, for example, polymeric glycols, gelatins, cocoa-butter or other low melting vegetable waxes or fats.

Typical transdermal formulations include a conventional aqueous or non-aqueous vehicle, for example, a cream, ointment, lotion or paste or are in the form of a medicated plastic, patch or membrane.

Typical compositions for inhalation are in the form of a solution, suspension or emulsion that can be administered in the form of an aerosol using a conventional propellant such as dichlorodifluoromethane or trichlorofluoromethane.

The therapeutically effective amount of a compound or pharmaceutical composition of the invention depends, in each case, upon several factors, e.g., the health, age, gender, size and condition of the subject to be treated, the intended mode of administration, and the capacity of the subject to incorporate the intended dosage form, among others. A therapeutically effective amount of an active agent is an amount sufficient to have the desired effect for the condition being treated. In a method of treating a subject with a condition treatable by chelating or sequestering a metal ion, a therapeutically effective amount of an active agent is, for example, an amount sufficient to reduce the burden of the metal in the subject, reduce the symptoms associated with the metal ion or prevent, inhibit or delay the onset and/or severity of symptoms associated with the presence of the metal. In a method of reducing oxidative stress in a subject in need of treatment thereof, a therapeutically effective amount of an active agent is, for example, an amount sufficient to reduce symptoms associated with oxidative stress or prevent, inhibit or delay the onset and/or severity of symptoms associated with oxidative stress. A typical total daily dose of a compound of the invention to be administered to a subject (assuming an average 70 kg subject) is from approximately 10 mg to 1.0 g.

An alternative approach to the syntheses of both (S)-4,5-dihydro-2-[2-hydroxy-4-(3,6,9-trioxadecyloxy)phenyl]-4-methyl-4-thiazolecarboxylic acid [(S)-4'-(HO)-DADFT-PE, 3] and [(S)-4,5-dihydro-2-[2-hydroxy-3-(3,6,9-trioxadecyloxy)phenyl]-4-methyl-4-thiazolecarboxylic acid [(S)-3'-(HO)-DADFT-PE, 9] is described below.

In the method described elsewhere [Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783], the synthesis of (S)-4,5-dihydro-2-[2-hydroxy-4-(3,6,9-trioxadecyloxy)phenyl]-4-methyl-4-thiazolecarboxylic acid [(S)-4'-(HO)-DADFT-PE, 3] is carried out: (S)-4'-(HO)-DADFT (1) was converted to its isopropyl ester in 99% yield. Alkylation of the 4'-hydroxyl using tri(ethylene glycol) monomethyl ether under Mitsunobu conditions (diisopropyl azodicarboxylate and triphenylphosphine in THF), filtration, and chromatography gave the isopropyl ester of 3 in 76% yield. Saponification of the ester furnished (S)-4'-(HO)-DADFT-PE (3) in 95% yield, providing an overall yield of 71%.

Figure 6:
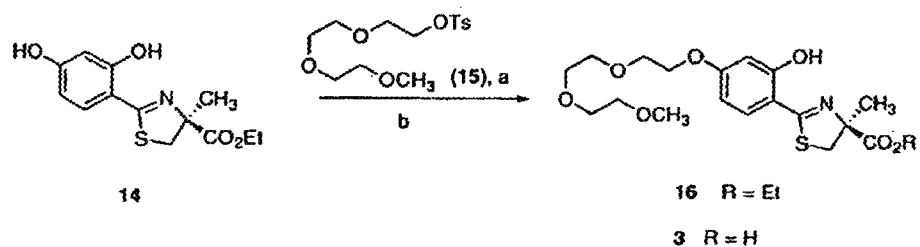
FIG. 6—Schemes 1 & 2. Syntheses of (S)-4,5-dihydro-2-[2-hydroxy-4-(3,6,9-trioxadecyloxy)phenyl]-4-methyl-4-thiazolecarboxylic acid [(S)-4'-(HO)-DADFT-PE] and [(S)-4,5-dihydro-2-[2-hydroxy-3-(3,6,9-trioxadecyloxy)phenyl]-4-methyl-4-thiazolecarboxylic acid [(S)-3'-(HO)-DADFT-PE], respectively
Figure 6:
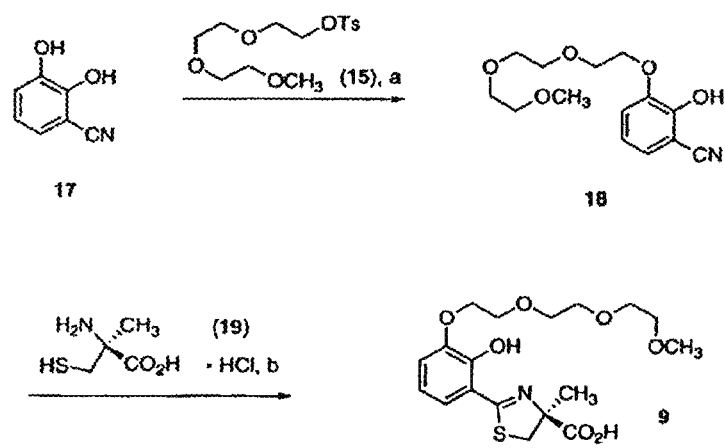

Alternatively, selective alkylation of the ethyl ester of (S)-4'-(HO)-DADFT (14) is accomplished by heating the tosylate of tri(ethylene glycol) monomethyl ether (15, 1.0 equiv) and potassium carbonate (2.0 equiv) in acetone, providing masked chelator 16 in 82% yield (FIG. 6; Scheme 1). Cleavage of ethyl ester 16 as before afforded (S)-4'-(HO)-DADFT-PE (3) in 95% yield. The new route to ligand 3 proceeds in greater overall yield, 78% vs. 71%; moreover, attachment of the polyether chain in Scheme 1 employs inexpensive reagents without formation of triphenylphosphine oxide and diisopropyl 1,2-hydrazinedicarboxylate, simplifying purification.

In the synthesis described above, the synthesis of (S)-4,5-dihydro-2-[2-hydroxy-3-(3,6,9-trioxadecyloxy)phenyl]-4-methyl-4-thiazolecarboxylic acid [(S)-3'-(HO)-DADFT-PE, 9] is carried out: (S)-2-(2,3-dihydroxyphenyl)-4,5-dihydro-4-methyl-4-thiazolecarboxylic acid, which was made in 88% yield from amino acid cyclization with the appropriate nitrile, was converted to its ethyl ester in 98% yield. However, the two remaining steps to chelator 9 proceeded in only 15% yield. The polyether chain was appended to the 3'-hydroxyl under Mitsunobu conditions, producing the ethyl ester of 9 in 25% yield. Ester hydrolysis furnished 9 in 60% yield after purification on a reverse phase column, providing an overall yield of 13%.

A more efficient syntheses of (S)-3'-(HO)-DADFT-PE (9) is presented in FIG. 6; Scheme 2. The less hindered phenolic group of 2,3-dihydroxybenzonitrile (17) [Bergeron, R. J., Wiegand, J., McManis, J. S., Weimar, W. R., Park, J.-H., Eiler-McManis, E., Bergeron, J. and Brittenham, G. M. Partition-Variant Desferrithiocin Analogues: Organ Targeting and Increased Iron Clearance. J. Med. Chem. 2005, 48, 821-831] was alkylated with tosylate 15 (1.3 equiv) and sodium hydride (2.1 equiv) in DMSO at room temperature, generating 18 in 70% chromatographed yield. Thus the triether chain has been attached in nearly three times the yield compared to the Mitsunobu coupling while avoiding the troublesome by-products. Cyclocondensation of nitrile 18 with (S)-alpha-methyl cysteine (19) in aqueous $CH_3OH$ buffered at pH 6 completed the synthesis of (S)-3'-(HO)-DADFT-PE (9) in 90% yield. Since the unusual amino acid 19 was not introduced until the last step of Scheme 2, the carboxyl group did not require protection. The overall yield to 9 is 63%, much higher than from the previous route.

Example 7

(S)-4,5-Dihydro-2-[2-hydroxy-4-(3,6,9-trioxadecyloxy) phenyl]-4-methyl-4-thiazolecarboxylic Acid (3). A solution of 50% (w/w) NaOH (10.41 mL, 199.5 mmol) in $CH_3OH$ (90 mL) was added to 16 (6.54 g, 15.3 mmol) in $CH_3OH$ (200 mL) with ice bath cooling. The reaction mixture was stirred at room temperature for 16 h, and the bulk of the solvent was removed by rotary evaporation. The residue was treated with dilute NaCl (150 mL) and was extracted with ether (3×150 mL). The basic aqueous phase was cooled in ice, acidified with 2 N HCl to a pH≈2, and extracted with EtOAc (4×100 mL). The EtOAc extracts were washed with saturated NaCl (200 mL) and were concentrated in vacuo. Drying under high vacuum furnished 5.67 g of 3[Bergeron, R. J., Wiegand, J., McManis, J. S., Vinson, J. R. T., Yao, H., Bharti, N. and Rocca, J. R. (S)-4,5-Dihydro-2-(2-hydroxy-4-hydroxyphenyl)-4-methyl-4-thiazolecarboxylic Acid Polyethers: A Solution to Nephrotoxicity. J. Med. Chem. 2006, 49, 2772-2783] (92%) as an orange oil: $[\alpha]^{25}$ +53.1° (c 0.98); $^1H$ NMR ($D_2O$) δ 1.76 (s, 3H), 3.35 (s, 3H), 3.54-3.61 (m, 3H), 3.64-3.72 (m, 4H), 3.74-3.78 (m, 2H), 3.90-3.94 (m, 2H), 3.96 (d, 1H, J=12.0), 4.25-4.29 (m, 2H), 6.53 (d, 1H, J=2.4), 6.64 (dd, 1H, J=9.0, 2.2), 7.61 (d, 1H, J=9.2); $^{13}C$ NMR ($D_2O$) δ 23.65, 39.56, 58.65, 68.34, 69.33, 70.07, 70.18, 70.44, 71.62, 77.58, 102.11, 106.72, 109.66, 134.67, 161.27, 167.07, 176.86, 180.70. Anal. ($C_{18}H_{25}NO_7S$) C, H, N.

Example 8

(S)-4,5-Dihydro-2-[2-hydroxy-3-(3,6,9-trioxadecyloxy) phenyl]-4-methyl-4-thiazolecarboxylic Acid (9). Compound 18 (7.63 g, 27.1 mmol), degassed 0.1 M pH 5.95 phosphate buffer (200 mL), 19 (6.98 g, 40.7 mmol), and $NaHCO_3$ (4.33 g, 51.5 mmol, in portions) were successively added to distilled, degassed $CH_3OH$ (200 mL). The reaction mixture, pH 6.2-6.6, was heated at 70° C. for 72 h. After cooling to room temperature, the bulk of the solvent was removed by rotary evaporation. The residue was dissolved in 8% $NaHCO_3$ (200 mL) and was extracted with $CHCl_3$ (3×100 mL). The aqueous portion was cooled in an ice water bath, acidified to pH≈1 with 5 N HCl, and extracted with EtOAc (4×100 mL). The EtOAc extracts were washed with saturated NaCl and were concentrated in vacuo. Drying under high vacuum furnished 9.74 g of 9 (90%) as an orange oil: $[\alpha]^{20}$ +61.9°; $^1H$ NMR ($D_2O$) δ 1.77 (s, 3H), 3.35 (s, 3H), 3.56-3.62 (m, 3H), 3.64-3.73 (m, 4H), 3.75-3.79 (m, 2H), 3.92-3.96 (m, 2H), 3.99 (d, 1H, J=11.6), 4.25-4.31 (m, 2H), 6.99 (t, 1H, J=8.2), 7.26-7.33 (m, 2H); $^{13}C$ NMR δ 24.52, 39.93, 59.07, 69.04, 69.83, 70.49, 70.64, 70.86, 71.97, 83.21, 116.33, 117.94, 118.50, 122.80, 147.67, 150.24, 172.38, 176.10; HRMS m/z calcd for $C_{18}H_{26}NO_7S$, 400.1429 (M+H); found, 400.1413.

Example 9

Ethyl (S)-4,5-Dihydro-2-[2-hydroxy-4-(3,6,9-trioxadecyloxy)phenyl]-4-methyl-4-thiazolecarboxylate (16). Flame activated $K_2CO_3$ (5.05 g, 36.6 mmol) followed by 15 (11.11 g, 34.9 mmol) in acetone (50 mL) were added to 14 (9.35 g, 33.2 mmol) in acetone (300 mL). The reaction mixture was heated at reflux for 3 days. Additional $K_2CO_3$ (4.59 g, 33.2 mmol) and 15 (2.12 g, 6.65 mmol) in acetone (5 mL) were added, and the reaction mixture was heated at reflux for 1 day. After cooling to room temperature, solids were filtered and the solvent was removed by rotary evaporation. The residue was dissolved in 1:1 0.5 M citric acid/saturated NaCl (320 mL) and was extracted with EtOAc (3×150 mL). The combined organic extracts were washed with distilled $H_2O$ (200 mL) and saturated NaCl (200 mL) and were concentrated in vacuo. Purification using flash column chromatography eluting with 50% EtOAc/petroleum ether generated 12.0 g of 16 (84%) as an oil: $[\alpha]^{23}$ +40.2 (c 1.09); $^1H$ NMR δ 1.30 (t, 3H, J=7.2) 1.66 (s, 3H), 3.19 (d, 1H, J=11.2), 3.38 (s, 3H), 3.54-3.57 (m, 2H), 3.64-3.70 (m, 4H), 3.72-3.76 (m, 2H), 3.81-3.88 (m, 3H), 4.12-4.17 (m, 2H), 4.20-4.28 (m, 2H), 6.46 (dd, 1H, J=8.8, 2.4), 6.49 (d, 1H, J=2.4), 7.28 (d, 1H, J=8.4), 12.69 (s, 1H); $^{13}C$ NMR δ 14.21, 24.58, 39.94, 59.17, 62.01, 67.65, 69.60, 70.69, 70.76, 70.98, 72.03, 83.22, 101.51, 107.41, 109.98, 131.77, 161.27, 163.09, 170.90, 172.95. Anal. ($C_{20}H_{29}NO_7S$) C, H, N.

Example 10

2-Hydroxy-3-(3,6,9-trioxadecyloxy)benzonitrile (18). Compound 17 (5.3 g, 39.2 mmol) was added to a suspension of 60% NaH (3.13 g, 78.2 mmol) in DMSO (60 mL) using oven-dried glassware. After the reaction mixture was stirred at room temperature for 1 h, 15 (12.49 g, 39.22 mmol) in DMSO (25 mL) was introduced. After 24 h of stirring at room temperature, the reaction mixture was poured with stirring into cold water (100 mL) and was extracted with $CHCl_3$ (3×100 mL). The aqueous phase was acidified to pH≈1 with 6 N HCl and was extracted with $CHCl_3$ (5×60 mL). The latter $CHCl_3$ extracts were concentrated in vacuo. Purification using column chromatography by gravity eluting with 10% $CH_3OH/CHCl_3$ gave 7.84 g of 18 (70%) as an oil: $^1H$ NMR δ 3.40 (s, 3H), 3.58-3.62 (m, 2H), 3.65-3.73 (m, 4H), 3.75-3.78 (m, 2H), 3.83-3.87 (m, 2H), 4.14-4.18 (m, 2H), 6.79-6.85 (m, 1H), 7.09 (dd, 1H, J=7.8, 1.6), 7.15-7.18 (m, 1H), 8.6 (s, 1H); $^{13}C$ NMR δ 57.25, 67.76, 67.85, 68.79, 68.92, 69.06, 70.36, 98.38, 115.44, 116.55, 118.51, 123.13, 145.98, 149.46; HRMS m/z calcd for $C_{14}H_{20}NO_5$, 282.134 (M+H); found, 282.135.

The description of the invention herein demonstrates the impact of introducing a 3,6,9-trioxadecyloxyl group at various positions of the desazadesferrithiocin (DADFT) aromatic ring on iron clearance and organ distribution is described. Three DADFT polyethers are evaluated: (S)-4,5-dihydro-2-[2-hydroxy-4-(3,6,9-trioxadecyloxy)phenyl]-4-methyl-4-thiazolecarboxylic acid [(S)-4'-(HO)-DADFT-PE, 3], (S)-4,5-dihydro-2-[2-hydroxy-5-(3,6,9-trioxadecyloxy) phenyl]-4-methyl-4-thiazolecarboxylic acid [(S)-5'-(HO)-DADFT-PE, 6], and (S)-4,5-dihydro-2-[2-hydroxy-3-(3,6,9-trioxadecyloxy)phenyl]-4-methyl-4-thiazolecarboxylic acid [(S)-3'-(HO)-DADFT-PE, 9]. The iron-clearing efficiency (ICE) in rodents and primates is shown to be very sensitive to which positional isomer is evaluated, as is the organ distribution in rodents. The polyethers had uniformly higher ICEs than their corresponding parent ligands in rodents, consistent with in vivo ligand-serum albumin binding studies. Ligand 9 is the most active polyether analogue in rodents and is also very effective in primates, suggesting a higher index of success in humans. In addition, this analogue is also shown to clear more iron in the urine of the primates than many of the other chelators.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, because numerous modifications will readily occur to those skilled in the art, it is not desired to limit the invention to the exact construction and operation illustrated and described, and accordingly, all suitable modifications and equivalents may be resorted to, falling within the scope of the invention.

The invention claimed is:
1. A method of treating a pathological condition in a subject comprising administering to the subject a therapeutically effective amount of a desazadesferrithiocin analog of formula:

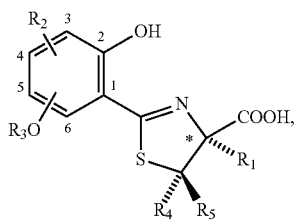

wherein:
$R_1$, $R_4$, and $R_5$ are the same or different and are H, straight or branched chain alkyl having up to 14 carbon atoms, or arylalkyl wherein the aryl portion is hydrocarbyl, the alkyl portion is straight or branched chain, and the arylalkyl group has up to 14 carbon atoms;
$R_2$ is H, straight or branched chain alkyl having up to 14 carbon atoms, alkoxy having up to 14 carbon atoms, or arylalkyl wherein the aryl portion is hydrocarbyl, the alkyl portion is straight or branched chain, and the arylalkyl group has up to 14 carbon atoms;
$R_3$ is $—[(CH_2)_n—O]_x—[(CH_2)_n—O]_y$-alkyl;
n is, independently, an integer from 1 to 8;
x is 3;
y is 0; and
$—OR_3$ occupies the 3-position on the phenyl ring; or a salt, hydrate, or solvate thereof;
wherein the pathological condition is metal overload, diabetes, liver disease, Friedreich ataxia (FRDA), heart disease, or radiation injury.

2. The method of claim 1, wherein $R_1$ is H or $—CH_3$.
3. The method of claim 1 wherein $R_2$ is H or $—OCH_3$.
4. The method of claim 1, wherein $—OR_3$ is $—O—[(CH_2)_2—O]_3—CH_3$.
5. The method of claim 1, wherein $R_4$ and $R_5$ are each H.
6. The method of claim 1, wherein $R_1$ is $—CH_3$.
7. The method of claim 1, wherein $R_2$ is H.
8. The method of claim 1, wherein each instance of n is 2.
9. The method of claim 1, wherein the salt is an alkali or alkaline earth metal salt.
10. The method of claim 1, wherein the salt is a sodium salt, potassium salt, magnesium salt, or calcium salt.
11. The method of claim 1, wherein the metal is trivalent.
12. The method of claim 1, wherein the pathological condition is metal overload.
13. The method of claim 12, wherein the metal overload is iron overload.
14. The method of claim 13, wherein the iron overload is primary hemochromatosis.
15. The method of claim 13, wherein the iron overload is secondary hemochromatosis.
16. The method of claim 13, wherein the iron overload is focal iron overload.
17. The method of claim 13, wherein the iron overload is thalassemia.
18. The method of claim 1, wherein the pathological condition is diabetes.
19. The method of claim 1, wherein the pathological condition is liver disease.
20. The method of claim 1, wherein the pathological condition is Friedreich ataxia (FRDA).
21. The method of claim 1, wherein the pathological condition is heart disease.
22. The method of claim 1, wherein the pathological condition is radiation injury.
23. A method of treating iron overload due to blood transfusions in a subject suffering therefrom comprising administering to the subject a therapeutically effective amount of a desazadesferrithiocin analog of formula:

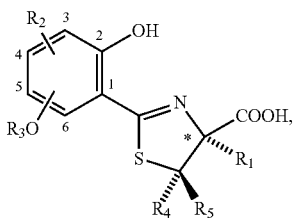

wherein:
$R_1$, $R_4$, and $R_5$ are the same or different and are H, straight or branched chain alkyl having up to 14 carbon atoms, or arylalkyl wherein the aryl portion is hydrocarbyl, the alkyl portion is straight or branched chain, and the arylalkyl group has up to 14 carbon atoms;
$R_2$ is H, straight or branched chain alkyl having up to 14 carbon atoms, alkoxy having up to 14 carbon atoms, or arylalkyl wherein the aryl portion is hydrocarbyl, the alkyl portion is straight or branched chain, and the arylalkyl group has up to 14 carbon atoms;
$R_3$ is $—[(CH_2)_n—O]_x—[(CH_2)_n—O]_y$-alkyl;
n is, independently, an integer from 1 to 8;
x is 3;
y is 0; and
$—OR_3$ occupies the 3-position on the phenyl ring; or a salt, hydrate, or solvate thereof.

24. The method of claim 23, wherein the desazadesferrithiocin analog is of the formula:

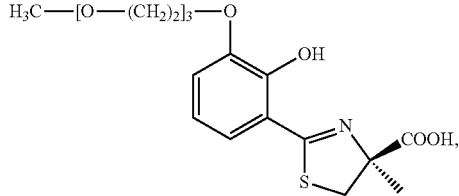

or a salt, hydrate, or solvate thereof.

25. The method of reducing oxidative stress in a subject comprising administering to the subject a therapeutically effective amount of a desazadesferrithiocin analog of formula:

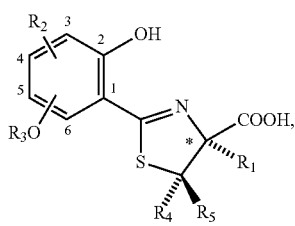

wherein:

R₁, R₄, and R₅ are the same or different and are H, straight or branched chain alkyl having up to 14 carbon atoms, or arylalkyl wherein the aryl portion is hydrocarbyl, the alkyl portion is straight or branched chain, and the arylalkyl group has up to 14 carbon atoms;

R₂ is H, straight or branched chain alkyl having up to 14 carbon atoms, alkoxy having up to 14 carbon atoms, or arylalkyl wherein the aryl portion is hydrocarbyl, the alkyl portion is straight or branched chain, and the arylalkyl group has up to 14 carbon atoms;

R₃ is —[(CH₂)$_n$—O]$_x$—[(CH₂)$_n$—O]$_y$-alkyl;

n is, independently, an integer from 1 to 8;

x is 3;

y is 0; and

—OR₃ occupies the 3-position on the phenyl ring; or a salt, hydrate, or solvate thereof.

26. The method of claim 12, wherein the metal overload is aluminum overload.

27. The method of claim 26, wherein the desazadesferrithiocin analog is of the formula:

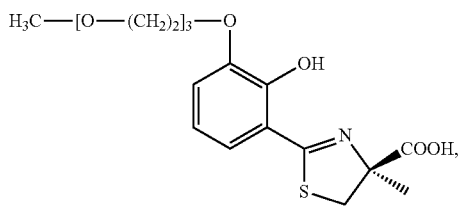

or a salt, hydrate, or solvate thereof.

28. The method of claim 20, wherein the desazadesferrithiocin analog is of the formula:

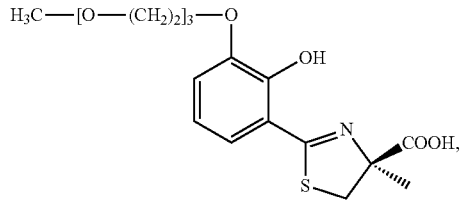

or a salt, hydrate, or solvate thereof.

29. The method of claim 23, wherein R₁ is H or —CH₃.
30. The method of claim 23 wherein R₂ is H or —OCH₃.
31. The method of claim 23, wherein —OR₃ is —O—[(CH₂)₂—O]₃—CH₃.
32. The method of claim 23, wherein R₄ and R₅ are each H.
33. The method of claim 23, wherein R₁ is —CH₃.
34. The method of claim 23, wherein R₂ is H.
35. The method of claim 23, wherein each instance of n is 2.
36. The method of claim 23, wherein the salt is an alkali or alkaline earth metal salt.
37. The method of claim 23, wherein the salt is a sodium salt, potassium salt, magnesium salt, or calcium salt.
38. The method of claim 25, wherein R₁ is H or —CH₃.
39. The method of claim 25 wherein R₂ is H or —OCH₃.
40. The method of claim 25, wherein —OR₃ is —O—[(CH₂)₂—O]₃—CH₃.
41. The method of claim 25, wherein R₄ and R₅ are each H.
42. The method of claim 25, wherein R₁ is —CH₃.
43. The method of claim 25, wherein R₂ is H.
44. The method of claim 25, wherein each instance of n is 2.
45. The method of claim 25, wherein the salt is an alkali or alkaline earth metal salt.
46. The method of claim 25, wherein the salt is a sodium salt, potassium salt, magnesium salt, or calcium salt.
47. The method of claim 25, wherein the desazadesferrithiocin analog is of the formula:

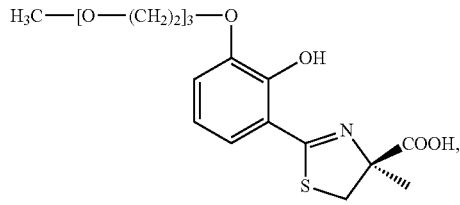

or a salt, hydrate, or solvate thereof.

* * * * *